US008956287B2

(12) United States Patent
Zdeblick et al.

(10) Patent No.: US 8,956,287 B2
(45) Date of Patent: Feb. 17, 2015

(54) PATIENT CUSTOMIZED THERAPEUTIC REGIMENS

(75) Inventors: Mark J. Zdeblick, Portola Valley, CA (US); Andrew Thompson, Portola Valley, CA (US); George M. Savage, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 665 days.

(21) Appl. No.: 12/299,303

(22) PCT Filed: May 2, 2007

(86) PCT No.: PCT/US2007/010688
§ 371 (c)(1),
(2), (4) Date: Oct. 31, 2008

(87) PCT Pub. No.: WO2007/130491
PCT Pub. Date: Nov. 15, 2007

(65) Prior Publication Data

US 2009/0076338 A1 Mar. 19, 2009

Related U.S. Application Data

(60) Provisional application No. 60/746,250, filed on May 2, 2006.

(51) Int. Cl.
*G06Q 50/00* (2012.01)
*A61B 5/00* (2006.01)
(Continued)

(52) U.S. Cl.
CPC ............ *G06F 19/3456* (2013.01); *A61B 5/073* (2013.01); *A61B 5/0028* (2013.01);
(Continued)

(58) Field of Classification Search
CPC ........... A61B 5/073; A61B 2560/0214; A61B 5/0026–5/0028; A61B 5/0002; A61B 2562/02; A61B 5/4833; A61J 3/002–3/10; H01M 4/02–4/0407; H01M 8/08; H01M 2220/10–2220/30; H01M 2300/0002–2300/0005; H04B 13/005; G06F 19/34–19/3475
USPC .................................. 705/2–3; 128/920–925
See application file for complete search history.

(56) References Cited

U.S. PATENT DOCUMENTS 3,589,943 A 6/1971 Grubb et al.
3,607,788 A 9/1971 Adolph
(Continued)

FOREIGN PATENT DOCUMENTS

CN 1991868 7/2007
CN 101005470 7/2007
(Continued)

OTHER PUBLICATIONS

McAdam, J. C. et al. “Synthesis, Structure, and Electronic Communication in Complexes Derived from RC2Co2(CO)6C2Co2(CO)6R”, Organometallics 1996, 15, 3935-3943.*
(Continued)

*Primary Examiner* — William Thomson
*Assistant Examiner* — Marie Archer
(74) *Attorney, Agent, or Firm* — K&L Gates LLP

(57) ABSTRACT

Methods, systems and compositions that allow for treating a patient according to a patient customized therapeutic regimen are provided. Embodiments of the invention include obtaining dosage administration information from a patient and using the same to tailor a therapeutic regimen for the patient. Embodiments of the invention further include preparing and forwarding to the patient physical pharmaceutical dosages based on the customized therapeutic regimen.

39 Claims, 4 Drawing Sheets

410 420 440 450 460 490 480 470 430 510 500 Special Delivery

(51) Int. Cl.

| | |
|---|---|
| ***A61B 5/07*** | (2006.01) |
| ***H01M 8/02*** | (2006.01) |
| ***G06Q 10/00*** | (2012.01) |
| ***G06Q 50/22*** | (2012.01) |
| *G06F 19/00* | (2011.01) |
| *H04B 13/00* | (2006.01) |
| *H01M 8/00* | (2006.01) |

(52) U.S. Cl.

CPC ............ *A61B5/0002* (2013.01); *H04B 13/005* (2013.01); *A61B 5/4833* (2013.01); *G06F 19/3418* (2013.01); *G06F 19/3475* (2013.01); *H01M 8/02* (2013.01); *G06Q 10/00* (2013.01); *G06Q 50/22* (2013.01); *H01M 2220/10* (2013.01); *Y10S 128/92* (2013.01); *Y10S 128/903* (2013.01)

USPC .................. 600/300; 705/2; 705/3; 128/920; 128/903; 340/870.07; 340/539.12; 340/573.1; 424/9.1; 424/408; 429/498; 600/302; 600/372

(56) References Cited

U.S. PATENT DOCUMENTS 3,628,669 A 12/1971 McKinnis et al.
3,642,008 A 2/1972 Bolduc
3,679,480 A 7/1972 Brown et al.
3,682,160 A 8/1972 Murata
3,719,183 A 3/1973 Schwartz
3,799,802 A 3/1974 Schneble, Jr. et al.
3,825,016 A * 7/1974 Lale et al. ...................... 607/29
3,828,766 A 8/1974 Krasnow
3,837,339 A 9/1974 Aisenberg et al.
3,893,111 A 7/1975 Cotter
3,944,064 A 3/1976 Bashaw et al.
3,967,202 A 6/1976 Batz
3,989,050 A 11/1976 Buchalter
4,017,856 A 4/1977 Wiegand
4,055,178 A 10/1977 Harrigan
4,062,750 A 12/1977 Butler
4,077,397 A 3/1978 Ellis
4,077,398 A 3/1978 Ellis
4,082,087 A 4/1978 Howson
4,090,752 A 5/1978 Long
4,105,023 A * 8/1978 Marchese et al. ............ 600/510
4,106,348 A 8/1978 Auphan
4,129,125 A 12/1978 Lester
4,166,453 A 9/1979 McClelland
4,239,046 A 12/1980 Ong
4,251,795 A 2/1981 Shibasaki et al.
4,269,189 A 5/1981 Abraham
4,331,654 A 5/1982 Morris
4,345,588 A 8/1982 Widder et al.
4,418,697 A 12/1983 Tama
4,425,117 A 1/1984 Hugemann et al.
4,439,196 A 3/1984 Higuchi
4,494,950 A 1/1985 Fischell
4,559,950 A 12/1985 Vaughan
4,564,363 A 1/1986 Bagnall et al.
4,578,061 A 3/1986 Lemelson
4,635,641 A 1/1987 Hoffman
4,654,165 A 3/1987 Eisenberg
4,663,250 A 5/1987 Ong et al.
4,669,479 A 6/1987 Dunseath
4,681,111 A 7/1987 Silvian
4,687,660 A 8/1987 Baker et al.
4,725,997 A 2/1988 Urquhart et al.
4,763,659 A 8/1988 Dunseath
4,767,627 A 8/1988 Caldwell et al.
4,784,162 A 11/1988 Ricks
4,793,825 A 12/1988 Benjamin et al.
4,809,705 A 3/1989 Ascher
4,844,076 A 7/1989 Lesho
4,876,093 A 10/1989 Theeuwes et al.
4,896,261 A 1/1990 Nolan
4,975,230 A 12/1990 Pinkhasov
4,987,897 A 1/1991 Funke
5,000,957 A 3/1991 Eckenhoff et al.
5,016,634 A 5/1991 Vock et al.
5,079,006 A 1/1992 Urquhart
5,167,626 A 12/1992 Casper
5,176,626 A 1/1993 Soehendra
5,245,332 A 9/1993 Katzenstein et al.
5,261,402 A 11/1993 DiSabito
5,263,481 A 11/1993 Axelgaard et al.
5,279,607 A 1/1994 Schentag et al.
5,281,287 A 1/1994 Lloyd
5,283,136 A 2/1994 Peled et al.
5,305,745 A 4/1994 Zacouto
5,318,557 A 6/1994 Gross
5,394,882 A 3/1995 Mawhinney
5,395,366 A 3/1995 D'Andrea et al.
5,436,091 A 7/1995 Shackle et al.
5,443,461 A 8/1995 Atkinson et al.
5,443,843 A 8/1995 Curatolo et al.
5,458,141 A 10/1995 Neil et al.
5,485,841 A 1/1996 Watkin et al.
5,511,548 A 4/1996 Riazzi et al.
5,567,210 A 10/1996 Bates et al.
5,596,302 A 1/1997 Mastrocola et al.
D377,983 S 2/1997 Sabri et al.
5,600,548 A 2/1997 Nguyen et al.
5,634,468 A 6/1997 Platt
5,645,063 A 7/1997 Straka, Jr.
5,705,189 A 1/1998 Lehmann et al.
5,720,771 A 2/1998 Snell
5,738,708 A 4/1998 Peachey et al.
5,740,811 A 4/1998 Hedberg
5,757,326 A 5/1998 Koyama et al.
5,792,048 A 8/1998 Schaefer
5,802,467 A 9/1998 Salazar
5,833,716 A 11/1998 Bar-Or
5,845,265 A 12/1998 Woolston
5,862,803 A 1/1999 Besson
5,862,808 A 1/1999 Albarello
5,868,136 A 2/1999 Fox
5,921,925 A 7/1999 Cartmell et al.
5,925,030 A 7/1999 Gross et al.
5,957,854 A 9/1999 Besson
5,963,132 A 10/1999 Yoakum et al.
5,974,124 A 10/1999 Schlueter, Jr. et al.
5,999,846 A 12/1999 Pardey et al.
6,023,631 A 2/2000 Cartmell et al.
6,038,464 A 3/2000 Axelgaard et al.
6,042,710 A 3/2000 Dubrow
6,047,203 A 4/2000 Sackner
6,076,016 A 6/2000 Feierbach
6,081,734 A 6/2000 Batz
6,083,248 A 7/2000 Thompson
6,090,489 A 7/2000 Hayakawa et al.
6,091,975 A 7/2000 Daddona et al.
6,095,985 A 8/2000 Raymond et al.
6,115,636 A 9/2000 Ryan
6,117,077 A 9/2000 Del Mar et al.
6,122,351 A 9/2000 Schlueter, Jr. et al.
6,141,592 A 10/2000 Pauly
6,149,940 A 11/2000 Maggi et al.
6,200,265 B1 3/2001 Walsh et al.
6,200,625 B1 3/2001 Beckett
6,204,764 B1 3/2001 Maloney
6,206,702 B1 3/2001 Hayden et al.
6,217,744 B1 4/2001 Crosby
6,231,593 B1 5/2001 Meserol
6,245,057 B1 6/2001 Sieben et al.
6,269,058 B1 7/2001 Yamanoi et al.
6,275,476 B1 8/2001 Wood
6,285,897 B1 9/2001 Kilcoyne et al.
6,287,252 B1 9/2001 Lugo
6,288,629 B1 9/2001 Cofino et al.
6,289,238 B1 9/2001 Besson
6,315,719 B1 11/2001 Rode et al.
6,342,774 B1 1/2002 Kreisinger et al.
6,344,824 B1 2/2002 Takasugi et al.
6,358,202 B1 3/2002 Arent

(56) References Cited

U.S. PATENT DOCUMENTS 6,364,834 B1 4/2002 Reuss
6,366,206 B1 4/2002 Ishikawa et al.
6,368,190 B1 4/2002 Easter et al.
6,371,927 B1 4/2002 Brune
6,374,670 B1 4/2002 Spelman
6,380,858 B1 4/2002 Yarin et al.
6,390,088 B1 5/2002 Noehl et al.
6,394,953 B1 5/2002 Devlin et al.
6,394,997 B1 5/2002 Lemelson
6,409,674 B1 6/2002 Brockway et al.
6,426,863 B1 7/2002 Munshi
6,432,292 B1 8/2002 Pinto et al.
6,440,069 B1 8/2002 Raymond et al.
6,441,747 B1 8/2002 Khair
6,453,199 B1 9/2002 Kobozev
6,471,645 B1 * 10/2002 Warkentin et al. ............ 600/300
6,477,424 B1 11/2002 Thompson et al.
6,482,156 B2 11/2002 Lliff
6,494,829 B1 12/2002 New et al.
6,496,705 B1 12/2002 Ng et al.
6,526,315 B1 2/2003 Inagawa
6,531,026 B1 3/2003 Takeichi et al.
6,544,174 B2 4/2003 West
6,564,079 B1 5/2003 Cory
6,572,636 B1 6/2003 Hagen et al.
6,577,893 B1 6/2003 Besson
6,579,231 B1 6/2003 Phipps
6,595,929 B2 7/2003 Stivoric
6,599,284 B2 7/2003 Faour et al.
6,605,038 B1 8/2003 Teller
6,605,046 B1 8/2003 Del Mar
6,609,018 B2 8/2003 Cory
6,612,984 B1 9/2003 Kerr
6,632,175 B1 10/2003 Marshall
6,632,216 B2 10/2003 Houzego et al.
6,635,279 B2 10/2003 Kolter et al.
6,643,541 B2 11/2003 Mok et al.
6,654,638 B1 11/2003 Sweeney
6,663,846 B1 12/2003 McCombs
6,673,474 B2 1/2004 Yamamoto
6,680,923 B1 1/2004 Leon
6,689,117 B2 2/2004 Sweeney et al.
6,694,161 B2 2/2004 Mehrotra
6,704,602 B2 3/2004 Berg et al.
6,720,923 B1 4/2004 Hayward et al.
6,738,671 B2 5/2004 Christophersom et al.
6,740,033 B1 5/2004 Olejniczak et al.
6,745,082 B2 6/2004 Axelgaard et al.
6,755,783 B2 6/2004 Cosentino
6,757,523 B2 6/2004 Fry
6,759,968 B2 7/2004 Zierolf
6,773,429 B2 8/2004 Sheppard et al.
6,800,060 B2 10/2004 Marshall
6,801,137 B2 10/2004 Eggers et al.
6,814,706 B2 11/2004 Barton et al.
6,822,554 B2 11/2004 Vrijens et al.
6,836,862 B1 12/2004 Erekson et al.
6,839,659 B2 1/2005 Tarassenko et al.
6,840,904 B2 1/2005 Goldberg
6,842,636 B2 1/2005 Perrault
6,845,272 B1 1/2005 Thomsen
6,864,780 B2 3/2005 Doi
6,879,810 B2 4/2005 Bouet
6,882,881 B1 4/2005 Lesser et al.
6,897,788 B2 5/2005 Khair et al.
6,909,878 B2 6/2005 Haller
6,922,592 B2 7/2005 Thompson et al.
6,928,370 B2 8/2005 Anuzis et al.
6,929,636 B1 8/2005 von Alten
6,937,150 B2 8/2005 Medema
6,942,616 B2 9/2005 Kerr
6,951,536 B2 10/2005 Yokoi
6,957,107 B2 10/2005 Rogers et al.
6,959,929 B2 11/2005 Pugnet et al.
6,968,153 B1 11/2005 Heinonen
6,987,965 B2 1/2006 Ng et al.
6,990,082 B1 1/2006 Zehavi et al.
7,002,476 B2 2/2006 Rapchak
7,004,395 B2 2/2006 Koenck
7,009,634 B2 3/2006 Iddan et al.
7,009,946 B1 3/2006 Kardach
7,013,162 B2 3/2006 Gorsuch
7,016,648 B2 3/2006 Haller
7,020,508 B2 3/2006 Stivoric
7,024,248 B2 4/2006 Penner et al.
7,031,745 B2 4/2006 Shen
7,031,857 B2 4/2006 Tarassenko et al.
7,039,453 B2 5/2006 Mullick
7,044,911 B2 5/2006 Drinan et al.
7,046,649 B2 5/2006 Awater et al.
7,072,725 B2 * 7/2006 Bristol et al. .................. 700/90
7,076,437 B1 7/2006 Levy
7,118,531 B2 10/2006 Krill
7,127,300 B2 10/2006 Mazar et al.
7,146,228 B2 12/2006 Nielsen
7,146,449 B2 12/2006 Do et al.
7,149,581 B2 12/2006 Goedeke et al.
7,154,071 B2 12/2006 Sattler et al.
7,155,232 B2 12/2006 Godfrey et al.
7,160,258 B2 1/2007 Imran
7,161,484 B2 1/2007 Tsoukalis
7,164,942 B2 1/2007 Avrahami
7,171,166 B2 1/2007 Ng et al.
7,171,177 B2 1/2007 Park et al.
7,171,259 B2 1/2007 Rytky
7,176,784 B2 2/2007 Gilbert et al.
7,187,960 B2 3/2007 Abreu
7,188,767 B2 3/2007 Penuela
7,194,038 B1 3/2007 Inkinen
7,206,630 B1 4/2007 Tarler
7,209,790 B2 4/2007 Thompson et al.
7,215,660 B2 5/2007 Perlman
7,215,991 B2 5/2007 Besson
7,218,967 B2 5/2007 Bergelson
7,231,451 B2 6/2007 Law
7,243,118 B2 7/2007 Lou
7,246,521 B2 7/2007 Kim
7,249,212 B2 7/2007 Do
7,252,792 B2 8/2007 Perrault
7,253,716 B2 8/2007 Lovoi et al.
7,261,690 B2 8/2007 Teller
7,270,633 B1 9/2007 Goscha
7,273,454 B2 9/2007 Raymond et al.
7,278,983 B2 * 10/2007 Ireland et al. .................. 604/66
7,285,090 B2 10/2007 Stivoric et al.
7,289,855 B2 10/2007 Nghiem
7,291,497 B2 11/2007 Holmes
7,292,139 B2 11/2007 Mazar et al.
7,294,105 B1 11/2007 Islam
7,307,544 B2 * 12/2007 Kim et al. ................ 340/870.07
7,313,163 B2 12/2007 Liu
7,317,378 B2 1/2008 Jarvis et al.
7,318,808 B2 1/2008 Tarassenko et al.
7,336,929 B2 2/2008 Yasuda
7,342,895 B2 3/2008 Serpa
7,346,380 B2 3/2008 Axelgaard et al.
7,349,722 B2 3/2008 Witkowski et al.
7,352,998 B2 4/2008 Palin
7,353,258 B2 4/2008 Washburn
7,357,891 B2 4/2008 Yang et al.
7,359,674 B2 4/2008 Markki
7,366,558 B2 4/2008 Virtanen et al.
7,368,190 B2 5/2008 Heller et al.
7,368,191 B2 5/2008 Andelman et al.
7,373,196 B2 5/2008 Ryu et al.
7,375,739 B2 5/2008 Robbins
7,376,435 B2 5/2008 McGowan
7,382,263 B2 6/2008 Danowski et al.
7,387,607 B2 6/2008 Holt
7,388,903 B2 6/2008 Godfrey et al.
7,389,088 B2 6/2008 Kim
7,392,015 B1 6/2008 Farlow
7,395,106 B2 7/2008 Ryu et al.
7,396,330 B2 7/2008 Banet

(56) References Cited

U.S. PATENT DOCUMENTS 7,404,968 B2 7/2008 Abrams et al.
7,413,544 B2 8/2008 Kerr
7,414,534 B1 * 8/2008 Kroll et al. ................ 340/573.1
7,414,543 B2 8/2008 Rye et al.
7,415,242 B1 8/2008 Ngan
7,424,268 B2 9/2008 Diener
7,424,319 B2 9/2008 Muehlsteff
7,427,266 B2 9/2008 Ayer et al.
7,471,665 B2 12/2008 Perlman
7,499,674 B2 3/2009 Salokannel
7,502,643 B2 3/2009 Farringdon et al.
7,505,795 B1 3/2009 Lim et al.
7,510,121 B2 3/2009 Koenck
7,512,448 B2 3/2009 Malick
7,515,043 B2 4/2009 Welch
7,519,416 B2 4/2009 Sula et al.
7,523,756 B2 4/2009 Minai
7,525,426 B2 4/2009 Edelstein
7,539,533 B2 5/2009 Tran
7,542,878 B2 6/2009 Nanikashvili
7,551,590 B2 6/2009 Haller
7,554,452 B2 6/2009 Cole
7,558,620 B2 7/2009 Ishibashi
7,575,005 B2 8/2009 Mumford
7,616,111 B2 11/2009 Covannon
7,616,710 B2 11/2009 Kim et al.
7,617,001 B2 11/2009 Penner et al.
7,639,473 B2 12/2009 Hsu et al.
7,640,802 B2 1/2010 King et al.
7,647,112 B2 1/2010 Tracey
7,647,185 B2 1/2010 Tarassenko et al.
7,653,031 B2 1/2010 Godfrey et al.
7,668,437 B1 2/2010 Yamada et al.
7,672,703 B2 3/2010 Yeo et al.
7,672,714 B2 3/2010 Kuo
7,673,679 B2 3/2010 Harrison et al.
7,678,043 B2 3/2010 Gilad
7,689,437 B1 3/2010 Teller et al.
7,697,994 B2 4/2010 VanDanacker et al.
7,720,036 B2 5/2010 Sadri
7,729,776 B2 6/2010 Von Arx et al.
7,733,224 B2 6/2010 Tran
7,736,318 B2 6/2010 Costentino
7,739,130 B2 * 6/2010 Surwit et al. ...................... 705/3
7,756,587 B2 7/2010 Penner et al.
7,779,614 B1 8/2010 McGonagle et al.
7,796,043 B2 9/2010 Euliano et al.
7,797,033 B2 9/2010 D'Andrea et al.
7,806,852 B1 10/2010 Jurson
7,809,399 B2 10/2010 Lu
7,844,341 B2 11/2010 Von Arx et al.
7,904,133 B2 3/2011 Gehman et al.
D639,437 S 6/2011 Bishay et al.
8,025,149 B2 9/2011 Sterry et al.
8,036,731 B2 10/2011 Kimchy et al.
8,073,707 B2 12/2011 Teller et al.
8,083,128 B2 12/2011 Dembo et al.
8,123,576 B2 2/2012 Kim
8,170,515 B2 5/2012 Le Reverend et al.
8,180,425 B2 5/2012 Selvitelli et al.
8,200,320 B2 6/2012 Kovacs
8,214,007 B2 7/2012 Baker et al.
8,224,667 B1 7/2012 Miller et al.
8,238,998 B2 8/2012 Park
8,249,686 B2 8/2012 Libbus et al.
8,258,962 B2 9/2012 Robertson et al.
8,285,356 B2 10/2012 Bly et al.
8,290,574 B2 10/2012 Felid et al.
8,301,232 B2 10/2012 Albert et al.
8,308,640 B2 11/2012 Baldus et al.
8,315,687 B2 11/2012 Cross et al.
8,369,936 B2 2/2013 Farringdon et al.
8,386,009 B2 2/2013 Lindberg et al.
8,389,003 B2 3/2013 Mintchev et al.
8,440,274 B2 5/2013 Wang
8,597,186 B2 12/2013 Hafezi et al.
2001/0027331 A1 10/2001 Thompson
2001/0031071 A1 10/2001 Nichols et al.
2001/0044588 A1 11/2001 Mault
2001/0051766 A1 12/2001 Gazdinski
2001/0056262 A1 12/2001 Cabiri et al.
2002/0002326 A1 1/2002 Causey, III
2002/0026111 A1 2/2002 Ackerman
2002/0032384 A1 3/2002 Raymond et al.
2002/0032385 A1 3/2002 Raymond et al.
2002/0040278 A1 4/2002 Anuzis et al.
2002/0077620 A1 6/2002 Sweeney et al.
2002/0132226 A1 9/2002 Nair
2002/0138009 A1 9/2002 Brockway et al.
2002/0192159 A1 * 12/2002 Reitberg ........................ 424/9.1
2002/0193669 A1 12/2002 Glukhovsky
2002/0193846 A1 12/2002 Pool et al.
2002/0198470 A1 12/2002 Imran et al.
2003/0017826 A1 1/2003 Fishman
2003/0023150 A1 1/2003 Yokoi et al.
2003/0028226 A1 2/2003 Thompson
2003/0063522 A1 4/2003 Sagar
2003/0065536 A1 4/2003 Hansen
2003/0076179 A1 4/2003 Branch et al.
2003/0083559 A1 5/2003 Thompson
2003/0126593 A1 7/2003 Mault
2003/0130714 A1 7/2003 Nielsen et al.
2003/0135128 A1 7/2003 Suffin et al.
2003/0135392 A1 7/2003 Vrijens et al.
2003/0152622 A1 8/2003 Louie-Helm et al.
2003/0158466 A1 8/2003 Lynn et al.
2003/0158756 A1 8/2003 Abramson
2003/0162556 A1 8/2003 Libes
2003/0164401 A1 9/2003 Andreasson et al.
2003/0167000 A1 9/2003 Mullick et al.
2003/0171791 A1 9/2003 KenKnight
2003/0171898 A1 9/2003 Tarassenko et al.
2003/0181788 A1 9/2003 Yokoi et al.
2003/0181815 A1 9/2003 Ebner et al.
2003/0185286 A1 10/2003 Yuen
2003/0187337 A1 10/2003 Tarassenko et al.
2003/0187338 A1 10/2003 Say et al.
2003/0195403 A1 10/2003 Berner et al.
2003/0213495 A1 11/2003 Fujita et al.
2003/0214579 A1 11/2003 Iddan
2003/0216622 A1 11/2003 Meron et al.
2003/0216625 A1 11/2003 Phipps
2003/0216666 A1 11/2003 Ericson et al.
2003/0216729 A1 11/2003 Marchitto
2003/0229382 A1 12/2003 Sun et al.
2003/0232895 A1 12/2003 Omidian et al.
2004/0008123 A1 1/2004 Carrender et al.
2004/0015132 A1 * 1/2004 Brown .......................... 604/131
2004/0018476 A1 1/2004 LaDue
2004/0019172 A1 1/2004 Yang et al.
2004/0034295 A1 2/2004 Salganicoff
2004/0049245 A1 3/2004 Gass
2004/0073095 A1 4/2004 Causey et al.
2004/0073454 A1 4/2004 Urquhart et al.
2004/0077995 A1 4/2004 Ferek-Petric
2004/0082982 A1 4/2004 Gord et al.
2004/0087839 A1 5/2004 Raymond et al.
2004/0092801 A1 5/2004 Drakulic
2004/0106859 A1 6/2004 Say et al.
2004/0111011 A1 6/2004 Uchiyama et al.
2004/0115517 A1 6/2004 Fukuda et al.
2004/0121015 A1 6/2004 Chidlaw et al.
2004/0122297 A1 6/2004 Stahmann et al.
2004/0148140 A1 7/2004 Tarassenko et al.
2004/0153007 A1 8/2004 Harris
2004/0167226 A1 8/2004 Serafini
2004/0167801 A1 8/2004 Say et al.
2004/0171914 A1 9/2004 Avni
2004/0176667 A1 * 9/2004 Mihai et al. .................. 600/300
2004/0193020 A1 9/2004 Chiba
2004/0193029 A1 9/2004 Glukhovsky
2004/0193446 A1 9/2004 Mayer et al.
2004/0199222 A1 10/2004 Sun et al.
2004/0215084 A1 10/2004 Shimizu et al.

(56) References Cited

U.S. PATENT DOCUMENTS

2004/1215084 10/2004 Shimizu et al.
2004/0218683 A1 11/2004 Batra
2004/0220643 A1 11/2004 Schmidt
2004/0224644 A1 11/2004 Wu
2004/0225199 A1 11/2004 Evanyk
2004/0253304 A1 12/2004 Gross et al.
2004/0258571 A1 12/2004 Lee et al.
2004/0260154 A1 12/2004 Sidelnik
2004/0267240 A1 12/2004 Gross et al.
2005/0017841 A1 1/2005 Doi
2005/0020887 A1 1/2005 Goldberg
2005/0021103 A1 1/2005 DiLorenzo
2005/0021370 A1 1/2005 Riff
2005/0024198 A1 2/2005 Ward
2005/0027205 A1 2/2005 Tarassenko et al.
2005/0038321 A1 2/2005 Fujita et al.
2005/0043634 A1 2/2005 Yokoi et al.
2005/0043894 A1 2/2005 Fernandez
2005/0054897 A1 3/2005 Hashimoto et al.
2005/0055014 A1 3/2005 Coppeta et al.
2005/0055242 A1* 3/2005 Bello et al. ........................ 705/2
2005/0062644 A1 3/2005 Leci
2005/0065407 A1 3/2005 Nakamura et al.
2005/0070778 A1 3/2005 Lackey
2005/0075145 A1 4/2005 Dvorak et al.
2005/0092108 A1 5/2005 Andermo
2005/0096514 A1 5/2005 Starkebaum
2005/0096562 A1 5/2005 Delalic et al.
2005/0101843 A1 5/2005 Quinn
2005/0101872 A1 5/2005 Sattler
2005/0115561 A1 6/2005 Stahmann et al.
2005/0116820 A1 6/2005 Goldreich
2005/0117389 A1 6/2005 Worledge
2005/0121322 A1 6/2005 Say et al.
2005/0131281 A1 6/2005 Ayer et al.
2005/0137480 A1 6/2005 Alt et al.
2005/0143623 A1 6/2005 Kojima
2005/0146594 A1 7/2005 Nakatani et al.
2005/0148883 A1 7/2005 Boesen
2005/0151625 A1 7/2005 Lai
2005/0154428 A1 7/2005 Bruinsma
2005/0156709 A1 7/2005 Gilbert et al.
2005/0165323 A1 7/2005 Montgomery
2005/0177069 A1 8/2005 Takizawa
2005/0182389 A1 8/2005 LaPorte
2005/0187789 A1 8/2005 Hatlestad et al.
2005/0192489 A1 9/2005 Marshall
2005/0197680 A1 9/2005 DelMain et al.
2005/0228268 A1 10/2005 Cole
2005/0234307 A1 10/2005 Heinonen
2005/0240305 A1 10/2005 Bogash et al.
2005/0245794 A1 11/2005 Dinsmoor
2005/0245839 A1 11/2005 Stivoric et al.
2005/0259768 A1 11/2005 Yang et al.
2005/0261559 A1 11/2005 Mumford
2005/0267556 A1 12/2005 Shuros et al.
2005/0267756 A1 12/2005 Schultz et al.
2005/0277912 A1 12/2005 John
2005/0277999 A1 12/2005 Strother et al.
2005/0280539 A1 12/2005 Pettus
2005/0285746 A1 12/2005 Sengupta
2005/0288594 A1 12/2005 Lewkowicz et al.
2006/0001496 A1 1/2006 Abrosimov et al.
2006/0028727 A1 2/2006 Moon et al.
2006/0036134 A1 2/2006 Tarassenko et al.
2006/0039977 A1* 2/2006 Tucker et al. ................. 424/473
2006/0047538 A1* 3/2006 Condurso et al. ................. 705/3
2006/0061472 A1 3/2006 Lovoi et al.
2006/0065713 A1 3/2006 Kingery
2006/0068006 A1 3/2006 Begleiter
2006/0074283 A1 4/2006 Henderson
2006/0074319 A1 4/2006 Barnes et al.
2006/0078765 A1 4/2006 Yang et al.
2006/0095091 A1 5/2006 Drew
2006/0095093 A1 5/2006 Bettesh et al.
2006/0100533 A1 5/2006 Han
2006/0109058 A1 5/2006 Keating
2006/0110962 A1 5/2006 Powell
2006/0122474 A1 6/2006 Teller et al.
2006/0122667 A1 6/2006 Chavan et al.
2006/0136266 A1 6/2006 Tarassenko et al.
2006/0142648 A1 6/2006 Banet
2006/0145876 A1 7/2006 Kimura
2006/0148254 A1 7/2006 McLean
2006/0149339 A1 7/2006 Burnes
2006/0155174 A1 7/2006 Glukhovsky et al.
2006/0155183 A1 7/2006 Kroecker
2006/0158820 A1 7/2006 Takiguchi
2006/0161225 A1 7/2006 Sormann et al.
2006/0179949 A1 8/2006 Kim
2006/0183992 A1 8/2006 Kawashima
2006/0183993 A1 8/2006 Horn
2006/0184092 A1 8/2006 Atanasoska et al.
2006/0204738 A1 9/2006 Dubrow et al.
2006/0210626 A1 9/2006 Spaeder
2006/0216603 A1 9/2006 Choi
2006/0218011 A1 9/2006 Walker
2006/0229053 A1 10/2006 Sivard
2006/0235489 A1 10/2006 Drew
2006/0243288 A1 11/2006 Kim et al.
2006/0247505 A1 11/2006 Siddiqui
2006/0253005 A1 11/2006 Drinan
2006/0255064 A1 11/2006 Donaldson
2006/0265246 A1 11/2006 Hoag
2006/0267774 A1 11/2006 Feinberg et al.
2006/0270346 A1 11/2006 Ibrahim
2006/0273882 A1 12/2006 Posamentier
2006/0280227 A1 12/2006 Pinkney
2006/0282001 A1 12/2006 Noel
2006/0289640 A1 12/2006 Mercure
2006/0293607 A1 12/2006 Alt
2007/0000776 A1 1/2007 Karube et al.
2007/0002038 A1 1/2007 Suzuki
2007/0006636 A1 1/2007 King et al.
2007/0008113 A1 1/2007 Spoonhower et al.
2007/0016089 A1 1/2007 Fischell et al.
2007/0027386 A1 2/2007 Such
2007/0027388 A1 2/2007 Chou
2007/0038054 A1 2/2007 Zhou
2007/0049339 A1 3/2007 Barak et al.
2007/0055098 A1 3/2007 Shimizu et al.
2007/0060797 A1 3/2007 Ball
2007/0060800 A1 3/2007 Drinan et al.
2007/0065363 A1* 3/2007 Dalal et al. ..................... 424/9.1
2007/0066929 A1 3/2007 Ferren et al.
2007/0073353 A1 3/2007 Rooney et al.
2007/0096765 A1 5/2007 Kagan
2007/0106346 A1 5/2007 Bergelson
2007/0123772 A1 5/2007 Euliano
2007/0129622 A1 6/2007 Bourget
2007/0130287 A1 6/2007 Kumar
2007/0135691 A1 6/2007 Zingelewicz et al.
2007/0135803 A1 6/2007 Belson
2007/0142721 A1 6/2007 Berner et al.
2007/0150026 A1* 6/2007 Bourget et al. ................. 607/46
2007/0156016 A1 7/2007 Betesh
2007/0160789 A1 7/2007 Merical
2007/0162089 A1 7/2007 Mosesov
2007/0162090 A1 7/2007 Penner
2007/0167495 A1 7/2007 Brown et al.
2007/0167848 A1 7/2007 Kuo et al.
2007/0168222 A1* 7/2007 Hoyme et al. .................... 705/2
2007/0173701 A1 7/2007 Al-Ali
2007/0179347 A1 8/2007 Tarassenko et al.
2007/0179371 A1 8/2007 Peyser et al.
2007/0180047 A1 8/2007 Dong et al.
2007/0185393 A1 8/2007 Zhou
2007/0191002 A1 8/2007 Ge
2007/0196456 A1 8/2007 Stevens
2007/0207793 A1 9/2007 Myer
2007/0207858 A1 9/2007 Breving
2007/0208233 A1 9/2007 Kovacs
2007/0213659 A1 9/2007 Trovato et al.
2007/0237719 A1 10/2007 Jones

(56) References Cited

U.S. PATENT DOCUMENTS

2007/0244370 A1 10/2007 Kuo et al.
2007/0249946 A1 10/2007 Kumar et al.
2007/0255198 A1 11/2007 Leong et al.
2007/0255330 A1 11/2007 Lee
2007/0270672 A1 11/2007 Hayter
2007/0279217 A1 12/2007 Venkatraman
2007/0282174 A1 12/2007 Sabatino
2007/0282177 A1 12/2007 Pilz
2007/0291715 A1 12/2007 Laroia et al.
2007/0299480 A1 12/2007 Hill
2008/0014866 A1 1/2008 Lipowski
2008/0015421 A1 1/2008 Penner
2008/0015494 A1 1/2008 Santini et al.
2008/0020037 A1 1/2008 Robertson et al.
2008/0021519 A1 1/2008 DeGeest
2008/0021521 A1 1/2008 Shah
2008/0027679 A1 1/2008 Shklarski
2008/0033273 A1 2/2008 Zhou
2008/0033301 A1 2/2008 Dellavecchia et al.
2008/0038588 A1 2/2008 Lee
2008/0039700 A1 2/2008 Drinan et al.
2008/0045843 A1 2/2008 Tsuji et al.
2008/0046038 A1 2/2008 Hill
2008/0051647 A1 2/2008 Wu et al.
2008/0051667 A1 2/2008 Goldreich
2008/0051767 A1 2/2008 Rossing et al.
2008/0058614 A1 3/2008 Banet
2008/0062856 A1 3/2008 Feher
2008/0065168 A1 3/2008 Bitton et al.
2008/0074307 A1 3/2008 Boric-Lubecke
2008/0077015 A1 3/2008 Botic-Lubecke
2008/0077028 A1 3/2008 Schaldach et al.
2008/0077188 A1 3/2008 Denker et al.
2008/0091089 A1 4/2008 Guillory et al.
2008/0091114 A1 4/2008 Min
2008/0097549 A1 4/2008 Colbaugh
2008/0097917 A1 4/2008 Dicks
2008/0099366 A1 5/2008 Niemic et al.
2008/0103440 A1 5/2008 Ferren et al.
2008/0114224 A1 5/2008 Bandy et al.
2008/0119705 A1 5/2008 Patel
2008/0119716 A1 5/2008 Boric-Lubecke
2008/0121825 A1 5/2008 Trovato
2008/0137566 A1 6/2008 Marholev
2008/0139907 A1 6/2008 Rao et al.
2008/0140403 A1 6/2008 Hughes et al.
2008/0146871 A1 6/2008 Arneson et al.
2008/0146889 A1 6/2008 Young
2008/0146892 A1 6/2008 LeBeouf
2008/0154104 A1 6/2008 Lamego
2008/0166992 A1 7/2008 Ricordi
2008/0175898 A1 7/2008 Jones et al.
2008/0183245 A1 7/2008 Van Oort
2008/0188837 A1 8/2008 Belsky et al.
2008/0194912 A1 8/2008 Trovato et al.
2008/0208009 A1 8/2008 Shklarski
2008/0214901 A1 9/2008 Gehman
2008/0214985 A1 9/2008 Yanaki
2008/0223936 A1 9/2008 Mickle et al.
2008/0243020 A1 10/2008 Chou
2008/0249360 A1 10/2008 Li
2008/0262320 A1 10/2008 Schaefer et al.
2008/0262336 A1 10/2008 Ryu
2008/0269664 A1 10/2008 Trovato et al.
2008/0275312 A1 11/2008 Mosesov
2008/0281636 A1 11/2008 Jung et al.
2008/0284599 A1 11/2008 Zdeblick et al.
2008/0288026 A1 11/2008 Cross et al.
2008/0288027 A1 11/2008 Kroll
2008/0294020 A1 11/2008 Sapounas
2008/0299197 A1 12/2008 Toneguzzo et al.
2008/0300572 A1 12/2008 Rankers
2008/0303638 A1 12/2008 Nguyen
2008/0306357 A1 12/2008 Korman
2008/0306359 A1 12/2008 Zdeblick et al.
2008/0306360 A1 12/2008 Robertson et al.
2008/0306362 A1 12/2008 Davis
2008/0311852 A1 12/2008 Hansen
2008/0312522 A1 12/2008 Rowlandson
2008/0316020 A1 12/2008 Robertson
2009/0009330 A1 1/2009 Sakama et al.
2009/0009332 A1 1/2009 Nunez et al.
2009/0024045 A1 1/2009 Prakash
2009/0024112 A1 1/2009 Edwards et al.
2009/0030293 A1 1/2009 Cooper et al.
2009/0030297 A1 1/2009 Miller
2009/0034209 A1 2/2009 Joo
2009/0043171 A1 2/2009 Rule
2009/0048498 A1 2/2009 Riskey
2009/0062634 A1 3/2009 Say et al.
2009/0062670 A1 3/2009 Sterling
2009/0069642 A1 3/2009 Gao
2009/0069655 A1 3/2009 Say et al.
2009/0069656 A1 3/2009 Say et al.
2009/0069657 A1 3/2009 Say et al.
2009/0069658 A1 3/2009 Say et al.
2009/0076340 A1 3/2009 Libbus et al.
2009/0076343 A1 3/2009 James
2009/0076397 A1 3/2009 Libbus et al.
2009/0087483 A1 4/2009 Sison
2009/0088618 A1 4/2009 Ameson
2009/0099435 A1 4/2009 Say et al.
2009/0105561 A1 4/2009 Boyden et al.
2009/0110148 A1 4/2009 Zhang
2009/0112626 A1 4/2009 Talbot
2009/0124871 A1 5/2009 Arshak
2009/0131774 A1 5/2009 Sweitzer
2009/0142853 A1 6/2009 Warrington et al.
2009/0149839 A1 6/2009 Hyde et al.
2009/0157113 A1 6/2009 Marcotte
2009/0157358 A1 6/2009 Kim
2009/0161602 A1 6/2009 Matsumoto
2009/0163789 A1 6/2009 Say et al.
2009/0171180 A1 7/2009 Pering
2009/0173628 A1 7/2009 Say et al.
2009/0177055 A1 7/2009 Say et al.
2009/0177056 A1 7/2009 Say et al.
2009/0177057 A1 7/2009 Say et al.
2009/0177058 A1 7/2009 Say et al.
2009/0177059 A1 7/2009 Say et al.
2009/0177060 A1 7/2009 Say et al.
2009/0177061 A1 7/2009 Say et al.
2009/0177062 A1 7/2009 Say et al.
2009/0177063 A1 7/2009 Say et al.
2009/0177064 A1 7/2009 Say et al.
2009/0177065 A1 7/2009 Say et al.
2009/0177066 A1 7/2009 Say et al.
2009/0182206 A1 7/2009 Najafi
2009/0182207 A1 7/2009 Riskey et al.
2009/0182212 A1 7/2009 Say et al.
2009/0182213 A1 7/2009 Say et al.
2009/0182214 A1 7/2009 Say et al.
2009/0182215 A1 7/2009 Say et al.
2009/0182388 A1 7/2009 Von Arx
2009/0187088 A1 7/2009 Say et al.
2009/0187089 A1 7/2009 Say et al.
2009/0187090 A1 7/2009 Say et al.
2009/0187091 A1 7/2009 Say et al.
2009/0187092 A1 7/2009 Say et al.
2009/0187093 A1 7/2009 Say et al.
2009/0187094 A1 7/2009 Say et al.
2009/0187095 A1 7/2009 Say et al.
2009/0187381 A1 7/2009 King et al.
2009/0192351 A1 7/2009 Nishino
2009/0192368 A1 7/2009 Say et al.
2009/0192369 A1 7/2009 Say et al.
2009/0192370 A1 7/2009 Say et al.
2009/0192371 A1 7/2009 Say et al.
2009/0192372 A1 7/2009 Say et al.
2009/0192373 A1 7/2009 Say et al.
2009/0192374 A1 7/2009 Say et al.
2009/0192375 A1 7/2009 Say et al.
2009/0192376 A1 7/2009 Say et al.
2009/0192377 A1 7/2009 Say et al.

(56) References Cited

U.S. PATENT DOCUMENTS

2009/0192378 A1 7/2009 Say et al.
2009/0192379 A1 7/2009 Say et al.
2009/0198115 A1 8/2009 Say et al.
2009/0198116 A1 8/2009 Say et al.
2009/0198175 A1 8/2009 Say et al.
2009/0203964 A1 8/2009 Shimizu et al.
2009/0203971 A1 8/2009 Sciarappa
2009/0203972 A1 8/2009 Heneghan
2009/0203978 A1 8/2009 Say et al.
2009/0204265 A1 8/2009 Hackett
2009/0210164 A1 8/2009 Say et al.
2009/0216101 A1 8/2009 Say et al.
2009/0216102 A1 8/2009 Say et al.
2009/0227204 A1 9/2009 Robertson et al.
2009/0227876 A1 9/2009 Tran
2009/0227940 A1 9/2009 Say et al.
2009/0227941 A1 9/2009 Say et al.
2009/0227988 A1 9/2009 Wood et al.
2009/0228214 A1 9/2009 Say et al.
2009/0231125 A1 9/2009 Baldus
2009/0234200 A1 9/2009 Husheer
2009/0243833 A1 10/2009 Huang
2009/0253960 A1 10/2009 Takenaka et al.
2009/0256702 A1 10/2009 Robertson
2009/0264714 A1 10/2009 Chou
2009/0264964 A1 10/2009 Abrahamson
2009/0265186 A1 10/2009 Tarassenko et al.
2009/0273467 A1 11/2009 Elixmann
2009/0277815 A1 11/2009 Kohl et al.
2009/0281539 A1 11/2009 Selig
2009/0292194 A1 11/2009 Libbus et al.
2009/0295548 A1 12/2009 Ronkka
2009/0296677 A1 12/2009 Mahany
2009/0301925 A1 12/2009 Alloro et al.
2009/0303920 A1 12/2009 Mahany
2009/0306633 A1 12/2009 Trovato et al.
2009/0312619 A1 12/2009 Say et al.
2009/0318303 A1 12/2009 Delamarche et al.
2009/0318761 A1 12/2009 Rabinovitz
2009/0318779 A1 12/2009 Tran
2009/0318783 A1 12/2009 Rohde
2009/0318793 A1 12/2009 Datta
2010/0001841 A1 1/2010 Cardullo
2010/0006585 A1 1/2010 Flowers et al.
2010/0010330 A1 1/2010 Rankers
2010/0033324 A1 2/2010 Shimizu et al.
2010/0049006 A1 2/2010 Magar
2010/0049012 A1 2/2010 Dijksman et al.
2010/0049069 A1 2/2010 Tarassenko et al.
2010/0056878 A1 3/2010 Partin
2010/0056891 A1 3/2010 Say et al.
2010/0056939 A1 3/2010 Tarassenko et al.
2010/0057041 A1 3/2010 Hayter
2010/0062709 A1 3/2010 Kato
2010/0063438 A1 3/2010 Bengtsson
2010/0063841 A1 3/2010 D'Ambrosia et al.
2010/0069002 A1 3/2010 Rong
2010/0069717 A1 3/2010 Hafezi et al.
2010/0081894 A1 4/2010 Zdeblick et al.
2010/0099967 A1 4/2010 Say et al.
2010/0099968 A1 4/2010 Say et al.
2010/0099969 A1 4/2010 Say et al.
2010/0100077 A1 4/2010 Rush
2010/0100078 A1 4/2010 Say et al.
2010/0106001 A1 4/2010 Say et al.
2010/0118853 A1 5/2010 Godfrey
2010/0139672 A1 6/2010 Kroll et al.
2010/0160742 A1 6/2010 Seidl et al.
2010/0168659 A1 7/2010 Say et al.
2010/0179398 A1 7/2010 Say et al.
2010/0185055 A1 7/2010 Robertson
2010/0191073 A1 7/2010 Tarassenko et al.
2010/0210299 A1 8/2010 Gorbachov
2010/0222652 A1 9/2010 Cho
2010/0228113 A1 9/2010 Solosko
2010/0233026 A1 9/2010 Ismagliov et al.
2010/0234706 A1 9/2010 Gilland
2010/0234715 A1 9/2010 Shin
2010/0234914 A1 9/2010 Shen
2010/0245091 A1 9/2010 Singh
2010/0249881 A1 9/2010 Corndorf
2010/0256461 A1 10/2010 Mohamedali
2010/0259543 A1 10/2010 Tarassenko et al.
2010/0268048 A1 10/2010 Say et al.
2010/0268049 A1 10/2010 Say et al.
2010/0268050 A1 10/2010 Say et al.
2010/0274111 A1 10/2010 Say et al.
2010/0280345 A1 11/2010 Say et al.
2010/0280346 A1 11/2010 Say et al.
2010/0295694 A1 11/2010 Kauffman et al.
2010/0298668 A1 11/2010 Hafezi et al.
2010/0298730 A1 11/2010 Tarassenko et al.
2010/0299155 A1 11/2010 Findlay et al.
2010/0312188 A1 12/2010 Robertson et al.
2010/0312580 A1 12/2010 Tarassenko et al.
2010/0332443 A1 12/2010 Gartenberg
2011/0004079 A1 1/2011 Al Ali et al.
2011/0009715 A1 1/2011 O'Reilly et al.
2011/0040203 A1 2/2011 Savage et al.
2011/0050431 A1 3/2011 Hood et al.
2011/0054265 A1 3/2011 Hafezi et al.
2011/0065983 A1 3/2011 Hafezi et al.
2011/0077660 A1 3/2011 Janik et al.
2011/0081860 A1 4/2011 Brown et al.
2011/0105864 A1 5/2011 Robertson et al.
2011/0124983 A1 5/2011 Kroll et al.
2011/0144470 A1 6/2011 Mazar et al.
2011/0224912 A1 9/2011 Bhavaraju et al.
2011/0230732 A1 9/2011 Edman et al.
2011/0237924 A1 9/2011 McGusty et al.
2011/0279963 A1 11/2011 Kumar et al.
2012/0024889 A1 2/2012 Robertson et al.
2012/0029309 A1 2/2012 Paquet et al.
2012/0062371 A1 3/2012 Radivojevic et al.
2012/0083715 A1 4/2012 Yuen et al.
2012/0089000 A1 4/2012 Bishay et al.
2012/0101396 A1 4/2012 Solosko et al.
2012/0197144 A1 8/2012 Christ et al.
2012/0214140 A1 8/2012 Brynelson et al.
2012/0265544 A1 10/2012 Hwang et al.
2012/0310070 A1 12/2012 Kumar et al.
2012/0316413 A1 12/2012 Liu et al.
2013/0030259 A1 1/2013 Thomsen et al.
2013/0057385 A1 3/2013 Murakami et al.
2013/0060115 A1 3/2013 Gehman et al.

FOREIGN PATENT DOCUMENTS

CN 201076456 6/2008
EP 0344939 12/1989
EP 1246356 10/2002
EP 1534054 5/2005
EP 1702553 9/2006
EP 1789128 5/2007
EP 2143369 1/2010
GB 2432862 6/2007
IL 172917 6/2010
JP 61017949 1/1986
JP 61072712 4/1986
JP 05-228128 9/1993
JP H0646539 2/1994
JP 09-330159 12/1997
JP 10-14898 1/1998
JP 2000-506410 5/2000
JP 2002-224053 8/2002
JP 2002263185 9/2002
JP 2002291684 10/2002
JP 2004-7187 1/2004
JP 2004134384 4/2004
JP 2004-313242 11/2004
JP 2005-073886 3/2005
JP 2005-304880 4/2005
JP 2005124708 5/2005
JP 2005-532841 11/2005

(56) References Cited

FOREIGN PATENT DOCUMENTS

| | | |
|---|---|---|
| JP | 2005-532849 | 11/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 2007159631 | 6/2007 |
| JP | 2007-313340 | 12/2007 |
| JP | 2008011865 | 1/2008 |
| JP | 2008501415 | 1/2008 |
| JP | 2009-061236 | 3/2009 |
| KR | 20020015907 | 3/2002 |
| KR | 20020061744 | 7/2002 |
| KR | 200609977523 | 7/2006 |
| KR | 927471 | 11/2009 |
| KR | 10-2012-09995 | 9/2012 |
| TW | 553735 | 9/2003 |
| TW | 200724094 | 7/2007 |
| WO | 8802237 | 4/1988 |
| WO | WO8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9714112 | 4/1997 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0100085 | 1/2001 |
| WO | 01/47466 | 7/2001 |
| WO | WO0149364 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | 2005/020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005082436 | 9/2005 |
| WO | WO2005083621 | 9/2005 |
| WO | WO2005110238 | 11/2005 |
| WO | WO2006021932 | 3/2006 |
| WO | WO2006027586 | 3/2006 |
| WO | WO2006028347 | 3/2006 |
| WO | WO2006035351 | 4/2006 |
| WO | 2006/055892 | 5/2006 |
| WO | 2006/055956 | 5/2006 |
| WO | WO2006046648 | 5/2006 |
| WO | WO2006075016 | 7/2006 |
| WO | WO2006100620 | 9/2006 |
| WO | 2006/104843 | 10/2006 |
| WO | WO2006109072 | 10/2006 |
| WO | 2006/116718 | 11/2006 |
| WO | 2006/127355 | 11/2006 |
| WO | WO2006119345 | 11/2006 |
| WO | 2007/001724 | 1/2007 |
| WO | 2007/001742 | 1/2007 |
| WO | 2007/013952 | 2/2007 |
| WO | 2007/014084 | 2/2007 |
| WO | 2007/021496 | 2/2007 |
| WO | WO2007014527 | 2/2007 |
| WO | 2007/027660 | 3/2007 |
| WO | 2007/028035 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | 2007130491 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007133526 | 11/2007 |
| WO | 2007/149546 | 12/2007 |
| WO | WO2007143535 | 12/2007 |
| WO | 2008/008281 | 1/2008 |
| WO | WO2008012700 | 1/2008 |
| WO | WO2008030482 | 3/2008 |
| WO | 2008/052136 | 5/2008 |
| WO | 2008/063626 | 5/2008 |
| WO | WO2008061138 | 5/2008 |
| WO | 2008/066617 | 6/2008 |
| WO | WO2008076464 | 6/2008 |
| WO | WO2008089232 | 7/2008 |
| WO | WO2008091683 | 7/2008 |
| WO | 2008/095183 | 8/2008 |
| WO | 2008/101107 | 8/2008 |
| WO | WO2008097652 | 8/2008 |
| WO | 2008/112577 | 9/2008 |
| WO | 2008/112578 | 9/2008 |
| WO | 20080120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | 2010019778 | 2/2010 |
| WO | 2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010115194 | 10/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |

(56) References Cited

FOREIGN PATENT DOCUMENTS

| | | |
|---|---|---|
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |

OTHER PUBLICATIONS

Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.*
Gilson, D.R. "Molecular dynamics simulation of dipole interactions", Department of Physics, Hull University, Dec. 2002, p. 1-43.
Li, P-Y, et al. "An electrochemical intraocular drug delivery device", Sensors and Actuators A 143 (2008) p. 41-48.
NPL_AntennaBasics.pdf, p. 1-3.
Santini, J.T. et al, "Microchips as controlled drug delivery-devices", Agnew. Chem. Int. Ed. 2000, vol. 39, p. 2396-2407.
Shawgo, R.S. et al. "BioMEMS from drug delivery", Current Opinion in Solid State and Material Science 6 (2002), p. 329-334.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Heydari et al., "Analysis of the PLL jitter due to power/ground and substrate noise"; IEEE Transactions on Circuits and Systems (2004) 51(12): 2404-16.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Yang et al., "Fast-switching frequency synthesizer with a discriminator-aided phase detector" IEEE Journal of Solid-State Circuits (2000) 35(10): 1445-52.
Mackay et al, Radio telemetering from within the body: Inside information is revealed by tiny transmitters that can be swallowed or implanted in man or animal. Science 1961;134(3486):1196-1202.
Mackay et al,. Endoradiosonde. Nature 1957;179(4572):1239-40, 179.
Zworkin, A 'radio pill.' Nature 1957;179:898.
Yao et al., Low Power Digital Communication in Implantable Devices Using Volume Conduction of Biological Tissues. Proceedings of the 28th IEEE, EMBC Annual International Conference 2006 (Aug. 30-Sep. 3); New York, USA.
McKenzie et al., Validation of a new telemetric core temperature monitor. J. Therm. Biol. 2004;29(7-8):605-11.
Tatbul et al., Confidence-based data management for personal area sensor networks. ACM International Conference Proceeding Series 2004;72.
Zimmerman, Personal Area Networks: Near-field intrabody communication. IBM Systems Journal 1996;35 (3-4):609-17.
Mini Mitter Co, Inc. 510(k) Premarket Notification Mini-Logger for Diagnostic Spirometer. Sep. 21, 1999.
Philips Respironics. 510(k) Premarket Notification for VitalSense. Apr. 22, 2004.
Mini Mitter Co, Inc. Actiheart. Traditional 510(k) Summary. Sep. 27, 2005.
Mini Mitter Co, Inc. VitalSense Integrated Physiological Monitoring System. Product Description.
Mini Mitter Co, Inc. VitalSense—Wireless Vital Signs Monitoring. Temperatures.com Mar. 31, 2009.
Mini Mitter Co, Inc. Noninvasive technology to help your studies succeed. Mini Mitter.com Mar. 31, 2009.
Barrie, Heidelberg pH capsule gastric analysis. Textbook of Natural Medicine, 1992, Pizzorno, Murray & Barrie.
Carlson et al., Evaluation of a non-invasive respiratory monitoring system for sleeping subjects. Physiological Measurement 1999;20(1):53.
Mojaverian et al., Estimation of gastric residence time of the Heidelberg capsule in humans: effect of varying food composition. Gastroenterology 1985;89(2):392-7.
Xiaoming et al., A telemedicine system for wireless home healthcare based on bluetooth and the internet. Telemedicine Journal and e-health 2004;10(S2):S110-6.
Arshak et al., A Review and Adaptation of Methods of Object Tracking to Telemetry Capsules IC-Med (2007) vol. 1, No. 1, Issue 1, pp. 35 of 46.
"ASGE Technology Status Evaluation Report: wireless capsule endoscopy" American Soc. for Gastrointestinal Endoscopy (2006) vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; (2003); abstract.
Brock, "Smart Medicine: The Application of Auto-ID Technology to Healthcare" Auto-ID Labs (2002) http://www.autoidlabs.org/uploads/media/MIT-AUTOID-WH-010.pdf.
Delvaux et al., "Capsule endoscopy: Technique and indications" Clinical Gastoenterology (2008) vol. 22, Issue 5, pp. 813-837.
Fawaz et al., "Enhanced Telemetry System using CP-QPSK Band—Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.
Given Imaging, "Agile Patency Brochure" http://www.inclino.no/documents/AgilePatencyBrochure_Global_GMB-0118-01.pdf;(N.D.) 4pp.
Gonzalez-Guillaumin et al., "Ingestible capsule for impedance and pH monitoring in the esophagus" IEEE Trans Biomed Eng. (2007) 54(12: 2231-6; abstract.
Greene, "Edible RFID microchip monitor can tell if you take your medicine" Bloomberg Businessweek (2010) 2 pp.; http://www.businessweek.com/idg/2010-03- 31/edible-rfid-microchip-monitor-can-tell-if-you-take-your-medicine.html.
Melanson, "Walkers swallow RFID pills for science" Engadget (2008); http://www.engadget.com/2008/07/29/walkers-swallow-rfid-pills-for-science/.
"New 'smart pill' to track adherence" E-Health-Insider (2010) http://www.e-health-insider.com/news/5910/new_'smart_pill'_monitors_medicines.
"RFID "pill" monitors marchers" RFID News (2008) http://www.rfidnews.org/2008/07/23/rfid-pill-monitors-marchers/.
"SensiVida minimally invasive clinical systems" Investor Presentation Oct. (2009) 28pp; http://www.sensividamedtech.com/SensiVidaGeneralOctober09.pdf.
Shrivas et al., "A New Platform for Bioelectronics-Electronic Pill", Cummins College, N. D.; http://www.cumminscollege.org/downloads/electronics_and_telecommunication/Newsletters/Current%20Newsletters.pdf.
"The SmartPill Wireless Motility Capsule" Smartpill, The Measure of GI Health; http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Swedberg, "University Team Sees Ingestible RFID Tag as a Boon to Clinical Trials" RFID Journal (2010) Apr. 27th; http://www.rfidjournal.com/article/view/7560/1.
University of Florida News "Rx for health: Engineers design pill that signals it has been swallowed" (2010) 2pp.; http://news.ufl.edu/2010/03/31/antenna-pill-2/.
Intromedic, MiroCam Innovative Capsule Endoscope Pamphlet. 8 pages. (http://www.intromedic.com/en/product/productInfo.asp).
Mini Mitter Co, Inc. 510(k) Premarket Notification for VitalSense. Apr. 22, 2004.
"Smartlife awarded patent for knitted transducer" Innovation in Textiles News: http://www.innovationintextiles.com/articles/208.php; 2pp. (2009).

(56) References Cited

OTHER PUBLICATIONS

Hotz "The Really Smart Phone" The Wall Street Journal, What They Know (2011); 6 pp.
ISFET—Ion Sensitive Field-Effect Transistor; Microsens S.A. pdf document. pp. 1-4.
Walkey, "MOSFET Struture and Processing"; 97.398* Physical Electronics Lecture 20; pp. 1-24.
Soper, S.A. et al. "Bio-Mems Technologies and Applications", Chapter 12, "MEMS for Drug Delivery", p. 325-346.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Hotz "The Really Smart Phone" The Wall Street Journal, What They Know (2011); 6 pages; http://online.wsj.com/article/SB10001424052748704547804578263261879848814.html?mod=djemTECH_t.
Bohidar et al., "Dielectric Behavior of Gelatin Solutions and Gels" Colloid Polym Sci (1998) 276:81-86.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Given Imaging, "Agile Patency Brochure" (2006) http://www.inclino.no/documents/AgilePatencyBrochure_Global_GMB-0118-01.pdf; 4pp.
ISFET—Ion Sensitive Field-Effect Transistor; Microsens S.A. pdf document. Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Kamada K., "Electrophoretic deposition assisted by soluble anode" Materials Letters 57 (2003) 2348-2351.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Roulstone, et al., "Studies on Polymer Latex Films: I. A study of latex film morphology" Polymer International 24 (1991) pp. 87-94.
Shin et al., "A Simple Route to Metal Nanodots and Nanoporous Metal Films"; Nano Letters, vol. 2, No. 9 (2002) pp. 933-936.
Soper, S.A. et al. "Bio-Mems Technologies and Applications", Chapter 12, "MEMS for Drug Delivery", p. 325-346 (2007).
U.S. Appl. No. 12/238,345, filed Sep. 25, 2008, Hooman et al., Non-Final Office Action mailed Jun. 13, 2011 22pp.
Walkey, "MOSFET Struture and Processing"; 97.398* Physical Electronics Lecture 20; First in Office Action dated Jun. 13, 2011 for U.S. Serial. No. 12/23/,345; 24 pp.
Wongmanerod et al., "Determination of pore size distribution and surface area of thin porous silicon layers by spectroscopic ellipsometry" Applied Surface Science 172 (2001) 117-125.
"PALO Bluetooth Baseband" PALO Bluetooth Resource Center (2002) Retrieved from internet Dec. 12, 2012 at URL: http://palowireless.com/bluearticles/baseband.asp; first Office Action dated Jan. 17, 2013 for EP08853901.0.
TRUTAG, Technologies, Inc., Spectral Microtags for Authentication and Anti-Counterfeiting; "Product Authentication and Brand Protection Solutions"; http://www.trutags.com/; downloaded Feb. 12, 2013; 1 page.
Lin et al., "Do Physiological Data Relate to Traditional Usability Indexes?" Proceedings of OZCHI 2005, Canberra, Australia (2005) 10 pp.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-6/04/0004; 2 pp.
Coury, L. "Conductance Measurement Part 1: Theory"; Current Separations, 18:3 (1999) p. 91-96.
Watson, et al., "Determination of the relationship between the pH and conductivity of gastric juice" Physiol Meas. 17 (1996) pp. 21-27.
Gaglani S. "Put Your Phone, Or Skin, on Vibrate" MedGadget (2012) http://medgadget.com/2012/03/put-your-phone-or-skin-on-vibrate.html 8pp.
Jimbo et al., "Gastric-fluid-utilized micro battery for micro medical devices" The Sixth International Workshop on Micro and Nanotechnology for Power Geneartion and Energy Conservation Applications, (2006) pp. 97-100.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Platt, D., "Modulation and Deviation" AE6EO, Foothills Amateur Radio Society; Oct. 26, 2007; 61 pp.
Rolison et al., "Electrically conductive oxide aerogels: new materials in electrochemistry" J. Mater. Chem. (2001) 1, 963-980.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Evanczuk, S., "PIC MCU software library uses human body for secure communications link" ; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pp.
Hoeksma, J. "New 'smart pill' to track adherence" E-Health-Insider; http://www.e-health-insider.com/news/5910/new_'smart_pill'_monitors_medicines; May 17, 2010 (2010); 1pp.
Owano, N., "Study proposes smart sutures with sensors for wounds" Phys.Org. http://phys.org/news/2012-08-smart-sutures-sensors-wounds.html; Aug. 26, 2012; 2pp.
Kim et al., "A Semi-Interpenetrating Network System for a Polymer Membrane"; Eur. Polym. J. vol. 33 No. 7; pp. 1009-1014 (1997).
Winter, J. et al. "The material properties of gelatin gels"; USA Ballistic Research Laboratories, Mar. 1975, p. 1-157.

* cited by examiner

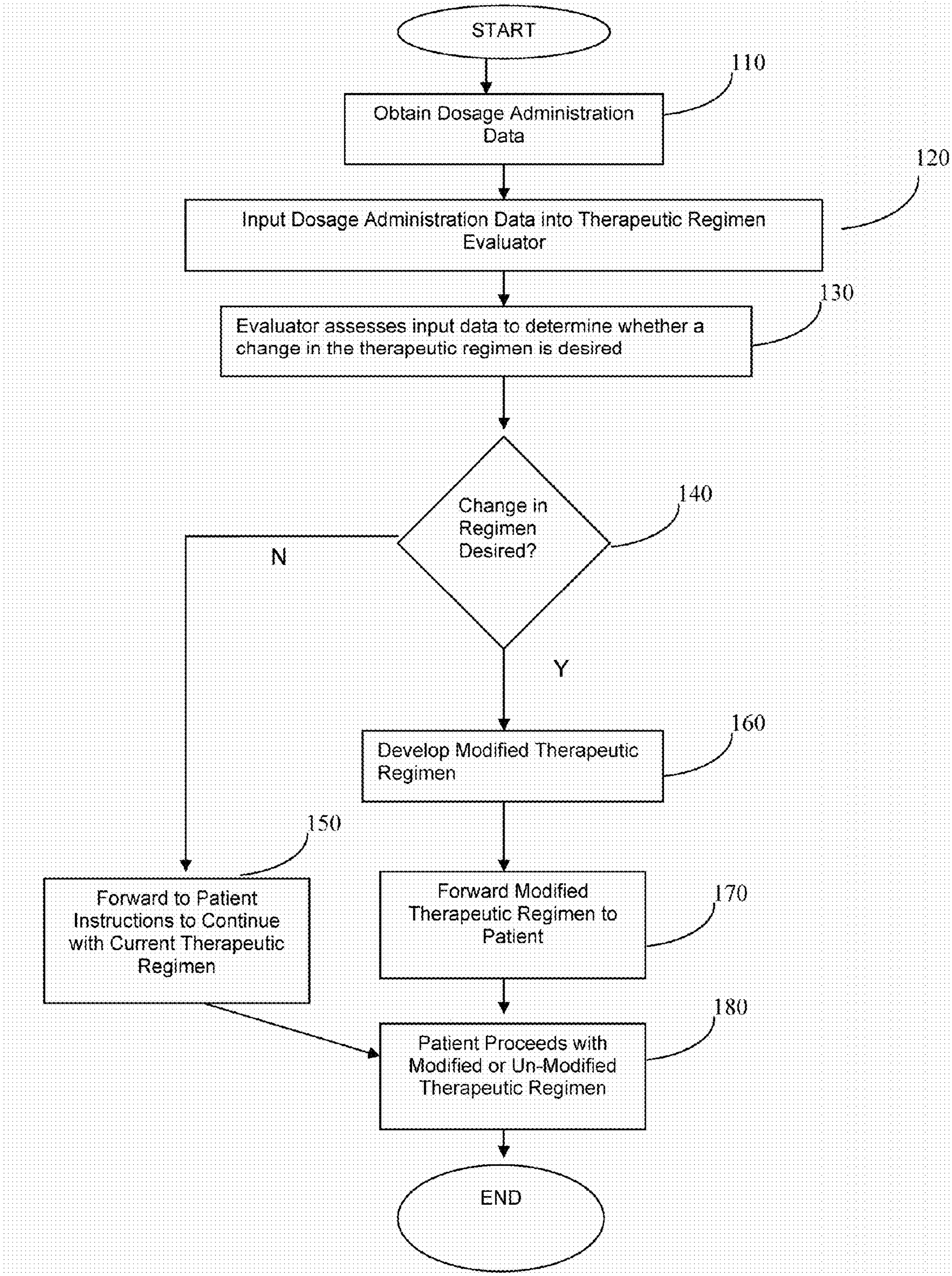
FIGURE 1
START
110
Obtain Dosage Administration Data
120
Input Dosage Administration Data into Therapeutic Regimen Evaluator
130
Evaluator assesses input data to determine whether a change in the therapeutic regimen is desired
140
Change in Regimen Desired?
N
Y
160
Develop Modified Therapeutic Regimen
150
Forward to Patient Instructions to Continue with Current Therapeutic Regimen
170
Forward Modified Therapeutic Regimen to Patient
180
Patient Proceeds with Modified or Un-Modified Therapeutic Regimen
END

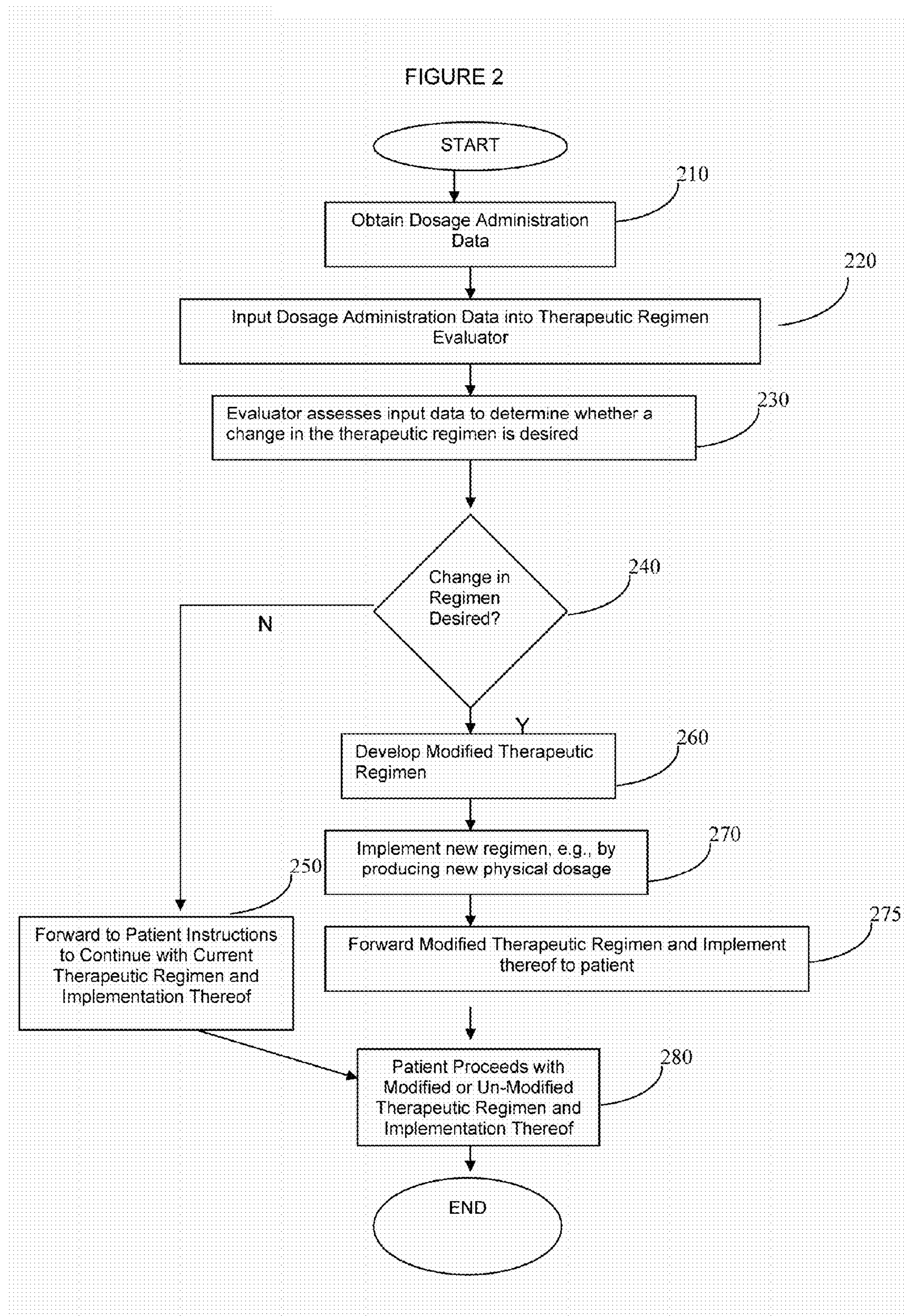
FIGURE 2
START
Obtain Dosage Administration Data
210
Input Dosage Administration Data into Therapeutic Regimen Evaluator
220
Evaluator assesses input data to determine whether a change in the therapeutic regimen is desired
230
Change in Regimen Desired?
240
N
Y
Develop Modified Therapeutic Regimen
260
Implement new regimen, e.g., by producing new physical dosage
270
Forward to Patient Instructions to Continue with Current Therapeutic Regimen and Implementation Thereof
250
Forward Modified Therapeutic Regimen and Implement thereof to patient
275
Patient Proceeds with Modified or Un-Modified Therapeutic Regimen and Implementation Thereof
280
END

PATIENT CUSTOMIZED THERAPEUTIC REGIMENS

CROSS-REFERENCE TO RELATED APPLICATIONS

Pursuant to 35 U.S.C. §119 (e), this application claims priority to the filing date of: U.S. Provisional Patent Application Ser. No. 60/746,250 filed May 2, 2006; the disclosure of which application is herein incorporated by reference.

INTRODUCTION

1. Field of the Invention

The present Invention relates generally to health care and particularly to therapeutic regimens. More specifically, the present invention relates to methods and systems for treating patients according to patient specific customized therapeutic regimens that can be adjusted as a treatment protocol progresses.

2. Background

Prescription medications are effective remedies for many patients when taken properly, e.g., according to instructions. However, prescription medications are generally taken according to predetermined dosing schedules that are developed using clinical data obtained from large patient populations. As such, when a health care practitioner determines that a patient will benefit from a given prescription medication, the health care practitioner generally assigns a standard dosage protocol to the patient, such as take once daily, take two times daily every 12 hours, etc.

While standard dosing regimens are based on clinical information taken from a large number of patients, such regimens do not take into account any physiological considerations that are unique to a given patient and may impact how a given pharmaceutical medication affects a particular patient. For example, such standard dosing schedules do not take into account the impact that any other medications which the patient may be taking may have on the activity of the prescribed medication. Furthermore, standard dosing schedules do not take into account any activity of an implanted medical device, e.g., a pacemaker, that may be present and operating on the patient. In addition, standard dosing schedules do not take into account any impact that non-compliance with the dosing schedule may have. Other parameters that are not accounted for in standard dosing schedules include a patient's daily anticipated activities, how a patient is subjectively feeling, etc.

Accordingly, standardized dosing regimens are not optimal dosing regimens for at least some patients that are prescribed medications for the treatment of a condition. Taking medications according to sub-optimal dosing regimens can have a variety of unwanted effects, including sub-optimal treatment, sub-optimal compliance, toxic side effects, and even death.

Therefore, there is a need for the development of better methods of determining therapeutic regimens for patients. Of particular interest would be the development of methods for determining patient customized therapeutic regimens, where such regimens are tailored for a particular patient. The present invention satisfies this, and other, needs.

SUMMARY

The present invention allows, for the first time, the development of patient specific customized therapeutic regimens, in which doses of therapeutic interventions, e.g., pharmaceutical intervention, are specifically tailored for a given patient, where the doses can be determined based on a number of different patient specific criteria, such as the impact of other medications a patient is taking, the anticipated daily activities of the patient, and the like. The present invention also allows for the ability to modify a given therapeutic regimen over time, e.g., to account for changes unique to a given patient, such as how the patient is responding to prior treatment, how the patient has complied with prior dosing schedules, etc.

Embodiments of the invention include methods in which dosage administration data (particularly in the form of confirmatory data for administration of a medical composition), such as compliance data, is obtained from the patient. This obtained confirmatory data are then evaluated, e.g., using automated decision tools, to determine whether a change in the therapeutic regimen that has been prescribed to the patient is desired. Based on this determination, the decision tool provides a recommendation. If a change is recommended, the therapeutic regimen for the patient may then be modulated in some manner. In certain embodiments, the methods further include implementation of the revised therapeutic regimen, e.g., in the form of preparation of a customized physical dosage according to the revised therapeutic regimen and forwarding of the same to the patient. Also provided are systems and programming for performing various steps of the subject methods.

BRIEF DESCRIPTION OF THE FIGURES

FIG. 1 presents a flow chart illustrating the process for developing a patient specific therapeutic regimen, in accordance with an embodiment of the present invention.

FIG. 2 presents a flow chart illustrating a variation of the process shown in FIG. 1, in which the modified therapeutic regimen is implemented by production of patient-specific physical pharmaceutical dosages, in accordance to one embodiment of the present invention.

DEFINITIONS

Figure 3:
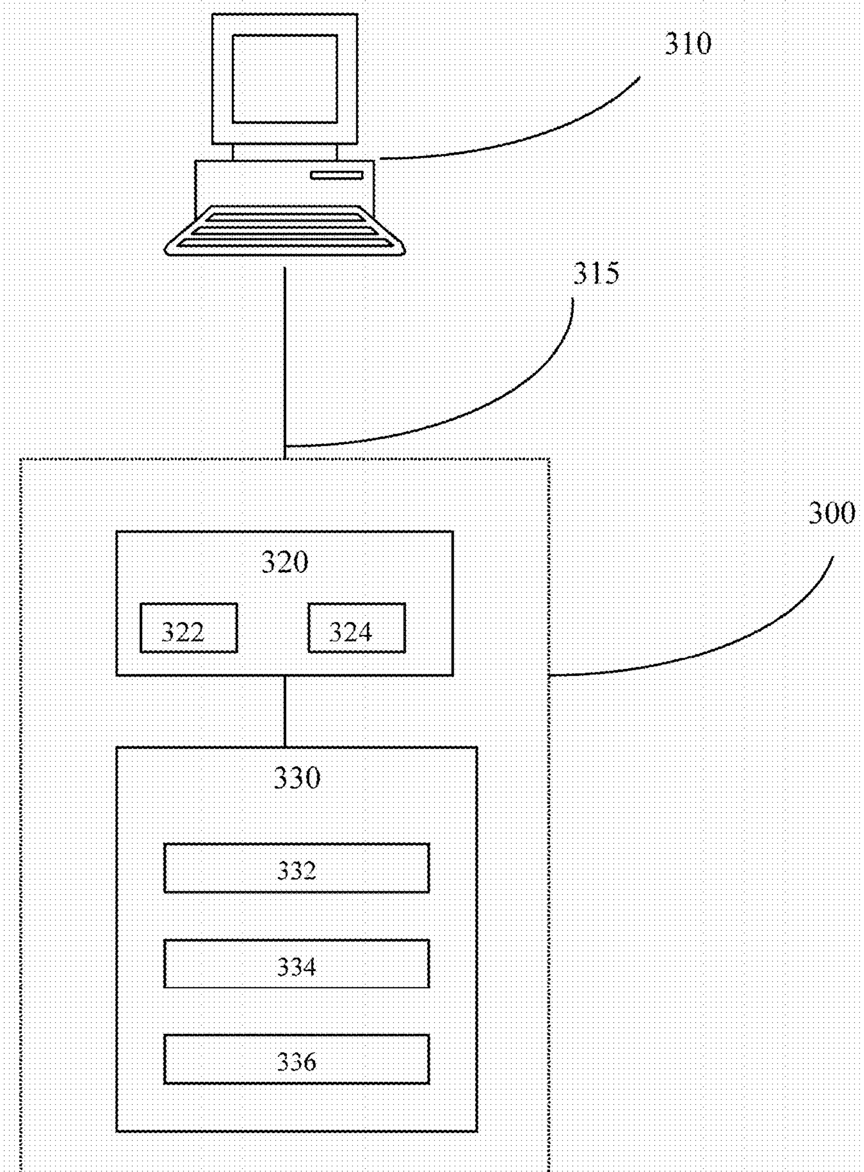
FIG. 3 provides an illustration of a specific embodiment of the present invention.

Unless defined otherwise, all technical and scientific terms used herein have the same meaning as commonly understood by one of ordinary skill in the art to which this invention belongs. Still, certain elements are defined below for the sake of clarity and ease of reference.

By "remote location," it is meant a location other than the location at which a referenced item is present, e.g., a location apart from a patient, such as another physical location, (e.g., office, lab, etc.) in the same city, another location in a different city, another location in a different state, another location in a different country, etc. As such, when one item is indicated as being "remote" from another, what is meant is that the two items are at least in different areas of the same room, such as in different rooms or different buildings, and may be at least one mile, ten miles, or at least one hundred miles apart.

"Communicating" information references transmitting the data representing that information as signals (e.g., electrical, optical, radio signals, etc.) over a suitable communication channel (e.g., a private or public network), for example, a Wide Area Network ("WAN"), telephone network, satellite network, or any other suitable communication channel, including the Internet, an Intranet, etc. Communicating may occur using any convenient communication module suitable for the type of communication channel used, such as a computer network card, a computer fax card or machine, or a telephone or satellite modem.

"Forwarding" an item refers to any means of getting that item from one location to the next, whether by physically transporting that item or otherwise (where that is possible) and includes, at least in the case of data, physically transporting a medium carrying the data or communicating the data, e.g., via ways described above.

The terms "system" and "computer-based system" refer to the hardware means, software means, and data storage means (e.g., a memory) used to practice aspects of the present invention. The minimum hardware of the computer-based systems of the present invention includes a central processing unit (CPU), input means, output means, and data storage means (e.g., a memory). A skilled artisan can readily appreciate that many computer-based systems are available which are suitable for use in the present invention. The data storage means may include any manufacture having a recording of the present information as described above, or a memory access means that can access such a manufacture.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

A "memory," "memory element" or "memory unit" refers to any device that can store information for subsequent retrieval by a processor, and may include magnetic or optical devices (such as a hard disk, floppy disk, CD, or DVD), or solid-state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

In certain embodiments, a system includes hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include the WINDOWS™ operating system, the SUN SOLARIS™ operating system, the LINUX™ operating system, the OS/400™ operating system, the COMPAQ TRU64 UNIX™ operating system, the SGI IRIX™ operating system, the SIEMENS RELIANT UNIX™ operating system, and others. The functional elements of system may also be implemented in accordance with a variety of software facilitators and platforms, as is known in the art.

DETAILED DESCRIPTION

The present invention provides the clinician important new tools in their therapeutic armamentarium—e.g., the ability to customize therapeutic regimens in a patient specific manner. The present invention allows therapeutic regimens to be developed and modified based on actual dosage administration information, i.e., confirmatory data for administration of a medical composition to a patient, which information can be supplemented with additional dosage relevant information, such as lifestyle information, etc. In this manner, patient specific customized optimal therapeutic regimens may be formulated by the clinician. By example, cardiac stimulating drugs can be titrated to the most appropriate dosages based on a number of factors, including actual compliance data, minimizing side effects such as cardiac muscle exhaustion and rebound effects among others, and optimizing both dosage and timing for each, individual patient.

Assessment of a range of alternate medications is made possible by the present invention without resort to awaiting overt clinical sequel of treatment, many of which can be seriously adverse. By example, positive effects would be quickly ascertainable without being obscured by more random factors. Negative responses, such as changes in blood pressure, would become clearly evident as drug related or independent above background physiologic variation. In one clinical arena, the present invention allows, in concert with other sensing devices, e.g., devices developed and owned by the assignee of the present application, the measurement and assessment of the cardiac response to those medications. These co-employed sensing devices can be those enumerated below, among others. Other sensing technology developed by some of the present inventors allows measurement of heart health and cardiac efficiency. Using these tools in concert with the present inventive methods and systems, the clinician will be able to compare the response of the heart and body to the administered pharmaceutical and make patient specific customized therapeutic regimen modifications to achieve and optimal patient specific therapeutic regimen.

In further describing the invention in greater detail, the methods are reviewed first in greater detail. Next, systems for implementing the methods are described. Finally, representative applications in which the methods find use are reviewed.

Methods

In one sense, the invention provides methods of treating a patient for a condition, where the condition may be a condition that benefits from some type of medical intervention, such as pharmaceutical intervention, nutritional/vitamin intervention, fluid intervention (e.g., dialysis), etc., where some form of medical composition is administered to a patient. The term "medical composition" is used broadly to refer a variety of different types of compositions that may be administered to a patient for an ultimate goal of somehow improving the health of the patient, where examples of medical compositions include, but are not limited to: pharmaceuticals or drugs (e.g., which may be available by prescription or over the counter), a vitamin and nutriceuticals, therapeutic fluids, such as infusates, e.g., saline, dialysates, etc., antacids, etc. For convenience of description only, the invention is now further described primarily in terms of pharmaceutical medical compositions. However, the invention is not so limited.

In practicing the methods of the invention, a first step is to obtain dosage administration data from a patient (i.e., confirmatory data for administration of a medical composition to a patient), where the patient is, in certain embodiments, on a therapeutic regimen. By "on a therapeutic regimen" is meant that the patient has been prescribed a therapeutic protocol in which the patient is administered, either self-administered or by a health care practitioner or another individual (or even the patient himself), a medical composition according to a dosing schedule, e.g., once every few hours, once a day, once every two days, once a week, etc.

In certain embodiments, the patient may be associated with an implantable medical device that is involved in administration of the medical composition, such as a cardiovascular device, e.g., diabetes care device, drug administration device, etc.

Dosage administration data that are obtained in this step of the methods is information about whether or not, as well as when, a patient has been administered (either through self administration or by another individual) a given therapeutic invention, e.g., activity of implantable device, a pharmaceutical dosage, etc. The dosage administration data are confirmatory data for administration of a medical composition to the patient. As the data are confirmatory, the data informs one that a particular composition has actually been administered to a patient. In certain embodiments, the confirmatory data are data that can only be generated when the medical composition actually contacts the patient, and therefore it is distinguishable from compliance data that may be generated from methods/systems which use a proxy for such contact, such as methods or systems that rely on patient recordation of administration, methods or systems that rely on smart packaging of medical compositions, etc. As such, dosage administration or confirmatory data employed in the methods of the invention may include pharmaceutical compliance data, which compliance data includes information on if, including when, a patient received a particular pharmaceutical dosage.

In certain embodiments, the confirmatory data are data that are produced by a first device and is transmitted to a second device, where both of said first and second devices are associated with the body of said patient. In these situations, a first device that is associated with the body generates or produces a signal (which may be a collection of individual data elements, such as bits) when the medical composition has been administered to the patient. The signal is then transmitted to a second device which receives, and may record, the signal. The second device is also associated with the body. By associated with the body is meant that the first and second devices are in contact with the body, either topically or inside of the body, e.g., ingested, implanted, etc., depending the particular nature of the first and second devices.

An example of where the first and second devices are associated with a body of patient is where the first and second devices are electrically coupled to the body of a patient. As the devices are electrically coupled to the body of the patient, the confirmatory data may be transmitted from the first device to the second device by establishing an electrical current between the first and second devices, where the body serves as the conductive medium through which the electrical current travels, and therefore provides for "Coulombic" communication between the first and second devices. Such embodiments are distinguished from devices that communicate with each other via radio frequency (RF).

Depending on the nature of the first and second devices, the electrical current may be one that is confined among the first and second devices and the body of the patient. For example, where the first device is a pharma-informatics enabled pharmaceutical dosage (described in greater detail below), and the second device is a personal health companion implanted inside of or topically present on the patient, the electrical current that is established upon transmission of the data may be confined to the first and second devices and the patient. Alternatively, the electrical current may be one that is confined between the first and second devices, wherein the first and second devices are capacitively coupled to a conductor or ground external to the patient. For example, where the first device is a smart parenteral delivery device and the second device is a personal health companion that is present on a surface of the patient, the first and second devices may be capacitively coupled to a convenient ground external to the patient and, and the confirmatory data transmitted from the first device to the second device using an electrical current established in the body of the patient.

The system of the first and second device may be viewed as one that generates confirmatory data by broadcasting an electronic signal from the first device while a medication is being administered to the patient, e.g., from the first device; conducting the confirmatory signal through the patient to a receiver associated with said patient, e.g., a personal health companion device implanted in the patient or topically applied to the patient; and recording the confirmatory signal by the second device.

To provide for improved reliability, though not necessary to practice all aspects of the invention, the confirmatory data may be obtained using a system of a first and second device that automatically generates, transmits, receives and records the confirmatory data. The phrase "automatically" refers to a situation where, apart from an initial setup, no human intervention is required for the confirmatory data to be obtained.

In certain embodiments, individually detectable smart dosages may be employed as the first devices described in the above systems which generate the confirmatory data. Examples of such smart dosages include, but are not limited to, those described in: U.S. Pat. No. 5,079,006 and published PCT Publication Nos. WO 2007/027660; WO 2007/021496; WO 2007/014084; WO 2007/013952; WO 2007/001742; WO 2007/001724; WO 2006/127355; WO 2006/104843; WO 2006/055892; WO 2001/047466; and WO 2005/020023; the disclosures of the monitoring devices and methods of these publications and the United States counterparts (e.g., priority applications) thereof, being specifically incorporated herein by reference.

Of particular interest in certain embodiments is the use of "smart" dosages that are activated upon contact with a target body location (e.g., the stomach), where activation occurs, for example, via completion of a power source. Such dosages may include identifiers associated with pharmaceutical compositions and provide information (i.e., confirmatory data) about when a patient is actually administered the dosage (e.g., by emitting a signal upon contact with a targeted physiological site, such as the stomach), such that the information obtained is not a proxy for the dosage administration but is, in fact, tied to actual administration of the dosage. Smart dosages of this type include those described in PCT application serial no. PCT/US2006/016370 titled "Pharma Informatics System" which was filed on Apr. 28, 2006 and published as WO 2006/116718 on Nov. 2, 2006; as well as the additional embodiments of such smart dosages as described in U.S. Provisional Application Ser. Nos. 60/866,581; 60/829,832; 60/887,780; 60/889,868; 60/889,870; 60/889,871; 60/894,171 and 60/894,167; the disclosures of which applications are herein incorporated by reference. Such dosages may be viewed as pharma-informatics enabled dosages.

Dosage compliance data can also be obtained using smart therapeutics systems, e.g., systems that provide specific identification and detection of beneficial agents or beneficial agents taken into the body through other methods, for example, through the use of a syringe, inhaler, infusion machine, dialysis machine, or other device that administers medicine. The smart therapeutics system can include a beneficial agent with a chip. The chip can contain information about the type of beneficial agent to be administered to the patient. Upon extracting the beneficial agent from the holding container, e.g., a vial, a signal can be sent from the vial to a chip within the syringe. The broadcasted signal can indicate the type of beneficial agent extracted from the vial. Upon injection into the patient, the information can be sent from the syringe to an information management database located in, on, or near the patient, e.g., a personal health companion device. The system can also notify the receiver about any therapies the patient is undergoing, such as dialysis. In this case, the dialysis machine, or an add-on module added to current dialysis machines, can be used to collect and transmit data about the dialysis being performed and parameters of the blood going out of and into the patient during dialysis. Upon successful detection and decoding of the transmitted signal, the receiver can activate an alert to let the nurse and/or other attending person or the patient that the receiver has successfully received information about the medication or therapy which was administered. Such systems are disclosed in U.S. Provisional Patent Application Nos. 60/819,750 filed Jul. 7, 2006 and 60/891,883 filed Feb. 27, 2007; the disclosures of which are herein incorporated by reference.

As indicated above, the second device may be a device configured to receive data transmitted through a body from the first device (and record and retransmit the data where desired), where the second device may be a personal health companion device that is configured to detect dosage administration, e.g., by a signal emitted by an identifier of a pharma-informatics enabled dosage formulation, such as described in pending provisional application Ser. No. 60/887,780 titled "Signal Receivers for Pharma-Informatics Systems"; the disclosure of which is herein incorporated by reference. As mentioned above, the personal health companion may be dimensioned for implantation and or topical application to a patient, where the device is dimensioned such that however it is associated with the patient it can be associated with the patient for extended periods of time, e.g., days, weeks, months, years or longer, without causing substantial if any discomfort to the patient.

In certain of the above described embodiments, the first device and the second device are different types of devices, e.g., where the first device may be associated with an active agent, such as where the first device is a smart dosage, and the second device is not associated with an active agent.

In certain embodiments, the methods include obtaining from the patient two or more sets of a confirmatory data over a given period of time, e.g., two or more sets of confirmatory data over a period of one day, one week, one month, one year, etc., depending on the particular regimen of the patient. While the two or more sets of confirmatory data may be generated from the same first device, in certain embodiments, e.g., where the first device is a pharma-informatics enabled dosage, e.g., such as a smart dosage described above, the first and second devices may be different dosages, e.g., different pills. As such, embodiments of the methods include obtaining an additional set of confirmatory data from at least a third device, e.g., a second pharmaceutical dosage which is separate from the first pharmaceutical dosage, where the same second device is employed regardless of how many additional first, third, etc., devices are employed.

In addition to dosage administration data, additional data may be obtained from the patient as desired. Types of additional patient data that may be obtained include, but are not limited to: physiological parameter data, e.g., as may be obtained using any convenient sensing device, including the sensors and systems developed by some of the inventors of the assignee of the present application and described in co-owned applications and patents, as referenced below; lifestyle data, such as historical information about the patient (e.g., the patients activities on a given day, how the patient was feeling, etc.); anticipated activities of the patient (e.g., whether or not the patient expects to exercise, whether or not the patient is feeling well, etc.); and the like.

Following obtainment of the dosage administration (i.e., confirmatory) data from the patient, e.g., where the patient may or may not be in a remote location such that obtainment of the data includes transmitting the data from a first location to a second location (for example over the internet) where the data are then evaluated, e.g., using a system as reviewed below, to determine when a change in the therapeutic regimen is desired and provide a recommendation based on the determination. This step of the methods may include inputting the data into a decision support tool (e.g., of an appropriate system) and obtaining from the decision support tool a recommendation based on the confirmatory data as to whether a change is the therapeutic regimen is desirable. The dosage administration data are assessed to identify whether, based on the information received from the patient, such as compliance data, physiological parameters and lifestyle data, any modification should be made to the therapeutic regimen in order to optimize the therapeutic regimen for the patient in some way. The data may be evaluated by a health care practitioner, e.g., manually or through use of any convenient decision tool, e.g., such as the system described below, that may include a database, algorithm, actionable interface (e.g., in the form of a graphical user interface (GUI)), outcome measure, etc.

The resultant recommendation based on this evaluation step may then be employed, e.g., by a health care professional, to determine whether the therapeutic regimen should be modulated in some manner. The determination is then communicated, e.g., by a health care practitioner, to the patient, where the determination may be in the form of an indication that no change in the therapeutic regimen should be made or that a change in the therapeutic regimen should be made. As such, the health care practitioner may inform the patient that no change in therapeutic regimen should be made and that the patient should continue to follow the therapeutic regimen as previously specified to the patient. Alternatively, the health care practitioner, following a recommendation from the evaluation step, may also forward to the patient a modified therapeutic regimen, e.g., in the form of instructions on how to change the regimen as previously specified to the patient.

The modulation of the therapeutic regimen, when made, may take a variety of different formats. For example, the modulation may take the form of a change in a pharmaceutical dosage regimen, e.g., in the amounts of active agent taken and/or the different types of active agents taken. The modulation may also take the form of a change in the activity of an implanted medical device. In addition, the modulation may include lifestyle alteration recommendations, e.g., instructions to refrain from exercise, instructions to engage in exercise, instructions to modify diet, etc.

In certain embodiments, the methods may further include implementation of change in a therapeutic regimen. This implementation may be manifested in a number of different ways. For example, this implementation may be in the form of the preparation of one or more actual, physical pharmaceutical dosages that will be used in the therapeutic regimen as modified. The phrase "physical pharmaceutical dosage" refers to the actual pharmaceutical composition(s) that is administered at any given time, e.g., the actual one or more pills that are administered at a given administration event. In one form of implementation, a modified therapeutic regimen that includes a selection of different active agents in specific amounts is implemented by collecting different compositions, e.g., pills, of the active agents into a set and forwarding the set to the patient. In another form of implementation, a combination of two or more active agents in amounts specified by a therapeutic regimen as described above are combined into a single composition, and the composition is then forwarded to the patient. For example, a given modified therapeutic regimen determined as described above may call for the administration of a first amount of pharmaceutical X, a second amount pharmaceutical Y and a third amount of pharmaceutical Z. A single composition is made, e.g., by a pharmaceutical composition manufacturer in response to instructions from a system, as reviewed in greater detail below, that includes all three different pharmaceuticals in the amounts specified. The three different amounts may be present in different compartments of an inert carrier, combined in a capsule, etc., as desired. The compositions of these embodiments may be manufactured at any point along a given supply chain, e.g., at the pharmaceutical agent manufacturer level, at a distributor level, at a retail (e.g., pharmacy) level or even at the customer level, e.g., by using a home device that prepares customized formulations from stock components. Implementation may also include modulation of the activity of an implanted device, such as a cardiac device, neurostimulatory device, etc., as may be desirable.

In certain embodiments, additional methods and systems of monitoring or tracking individual dosages or collections of dosages may be employed in conjunction, with the methods and systems of the present invention. For example, "smart" package devices (i.e., pharmaceutical compliance packages) which record when a patient obtains a dosage from the package and thereby provides a proxy for the administration of the dosage to the patient may be employed. Examples of such "smart" packaging devices and methods are found in, but not limited to: smart drug dispensers as disclosed in U.S. Pat. Nos. 4,360,125; 4,768,176; 4,768,177; 5,200,891; 5,642,731; 5,752,235 and 5,954,641; the disclosures of which are herein incorporated by reference. Alternatively or in addition, RFID/barcode approaches may be employed to provide additional confirmation or tracking information between a source of pharmaceutical dosages and patient.

Other sources of dosage compliance data include, but are not limited to, patient data recordation, e.g., via input into a compliance recordation program, etc. Dosage administration data can also include implantable medical device activity data, such as pacemaker activity data, where such activity may be monitored using any convenient system, including the system described in published PCT Application Publication No. WO 2007/028035 titled "Implantable Zero-Wire Communications System", the disclosure of which is herein incorporated by reference.

Such additional sources of information may be employed in conjunction with the methods of invention, where desired.

FIGS. 1 and 2 provide flow charts of two different embodiments of the methods described above. In FIG. 1, the first step 110 of the exemplified method is to obtain dosage administration data, such as pharmaceutical compliance data, as reviewed above. Next, at step 120 the obtained dosage administration data are input into a therapeutic regimen evaluator, e.g., as described in greater detail below. Following step 120, the evaluator assesses at step 130 the input data to determine whether a change in the therapeutic regimen is desired. At decision box 140, if a change is the regimen is not recommended, instructions are forwarded to the patient to continue with the current therapeutic regimen, as shown at step 150. However, if a change in the regimen is recommended at decision box 140, a modified therapeutic regimen, e.g., in the form of a changed pharmaceutical dosage regimen and/or implanted medical device activity regimen, is developed at step 160. The developed modulated pharmaceutical dosage regimen is then forwarded to the patient at step 170. Finally, the patient proceeds by continuing to follow the prior therapeutic regimen or adopting the modified regimen, as shown at step 180.

FIG. 2 provides a modified version of the protocol shown in FIG. 1, where the method includes an implementation of the modified therapeutic regimen. In FIG. 2, the first step 210 of the exemplified method is to obtain dosage administration data, such as pharmaceutical compliance data, as reviewed above. Next, at step 220 the obtained dosage administration data are input into a therapeutic regimen evaluator, e.g., as described in greater detail below. Following step 220, the evaluator assesses at step 230 the input data to determine whether a change in the therapeutic regimen is desired. At decision box 240, if a change is the regimen is not recommended, instructions are forwarded to the patient to continue with the current therapeutic regimen, as shown at step 250. At step 250, instructions are also sent to the patient to continue with the implementation of the prior therapeutic regimen, e.g., by taking the same pharmaceutical compositions according to the same dosing schedule, etc. However, if a change in the regimen is recommended at decision box 240, a modified therapeutic regimen, e.g., in the form of a changed pharmaceutical dosage regimen and/or implanted medical device activity regimen, is developed at step 260. The resultant modified therapeutic regimen is implemented as desired, e.g., by fabricating a physical pharmaceutical dosage (as described above) at step 270. The developed modified pharmaceutical dosage regimen and implementation thereof is then forwarded to the patient at step 275. Finally, the patient proceeds by continuing to follow the prior therapeutic regimen or adopting the modified regimen, along with the implementation thereof, as shown at step 280.

Systems

Also provided by the subject invention are systems that may be used to perform on or more aspects of the methods, such as the data evaluation step, e.g., as described above. In certain embodiments, the systems include a decision tool, e.g., in the form of a processor accessing a database and running an appropriate algorithm, which may take the form of a data evaluation module, which serves as a therapeutic regimen evaluator to assess the input data and provide a recommendation of whether or not a change is desired.

In the process schematically depicted in FIG. 1, a data evaluation module is employed as a therapeutic regimen evaluator to assess the input data and generate a recommendation as to whether or not the regimen should be changed. As such, the data evaluation module performs the function of receiving the input information and generating the regimen recommendation information in response thereto.

The data evaluation module employed in the subject methods may include a collection dosage administration data (e.g., compliance data) element and regimen recommendation linked data element stored in a memory, such as a database. The data elements of the module may be organized in any convenient manner. The content of the data evaluation module may be controlled using any convenient protocol. In certain embodiments, the content may be maintained by a single entity, e.g., where the entity initially creates the content and then updates the content periodically. Embodiments of the modules include updated modules in which the content of the module has been updated one or more times following its manufacture, e.g., two or more times, 5 or more times, 10 or more times, 50 or more times, 100 or more times, 1000 or more times, etc., where the updated content may be any of a variety of different types of information.

An embodiment of a system that includes a data evaluation module is shown in FIG. 3. In FIG. 3, system 300 includes communications module 320 and processing module 330, where each module may be present on the same or different platforms, e.g., servers, as is known in the art. The communications module includes an input manager 322 and output manager 324 functional elements. Input manager 322 receives information, e.g., sample identifier information, from a user e.g., locally or from a remote location (such as over the Internet). Input manager 322 processes and forwards this information to the processing module 330. Output manager 324 provides information assembled by processing module 330, e.g., a modified therapeutic regimen, to a user. The communications module 320 may be operatively connected to a user computer 310 by communications element 315, which element provides a vehicle for a user to interact with the system 300. User computer 310, shown in FIG. 3, may be a computing device specially designed and configured to support and execute any of a multitude of different applications. Computer 310 also may be any of a variety of types of general-purpose computers such as a personal computer, network server, workstation, or other computer platform now or later developed.

As reviewed above, the systems include various functional elements that carry out specific tasks on the platforms in response to information introduced into the system by one or more users. In FIG. 3, elements 332, 334 and 336 represent three different functional elements of processing module 330. At least one of the functional elements 332 of processing module 330 is a functionality for assessing the dosage administration data and providing a determination as to whether a change in at therapeutic dosage regimen is desired, and is conveniently referred to herein as the therapeutic regimen evaluator. Additional functional elements that may be present include, but are not limited to, elements for determining modified therapeutic regimens, etc. In certain embodiments, the systems include one or more implantable devices, which may have therapeutic (such as electrostimulatory) and/or sensory activity. Such sensors and systems include, but are not limited to, those described in various applications assigned to the assignee of the present application, where such applications include, but are not limited to: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324,196 titled "Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368,259 titled: "Fiberoptic Tissue Motion Sensor"; International Application No. PCT/US2004/041430 titled: "Implantable Pressure Sensors"; U.S. patent application Ser. No. 11/249,152 entitled "Implantable Doppler Tomography System," and claiming priority to: U.S. Provisional Patent Application No. 60/617,618; International Application Serial No. PCT/USUS05/39535 titled "Cardiac Motion Characterization by Strain Gauge". These applications are incorporated in their entirety by reference herein.

REPRESENTATIVE EMBODIMENT

Figure 4:
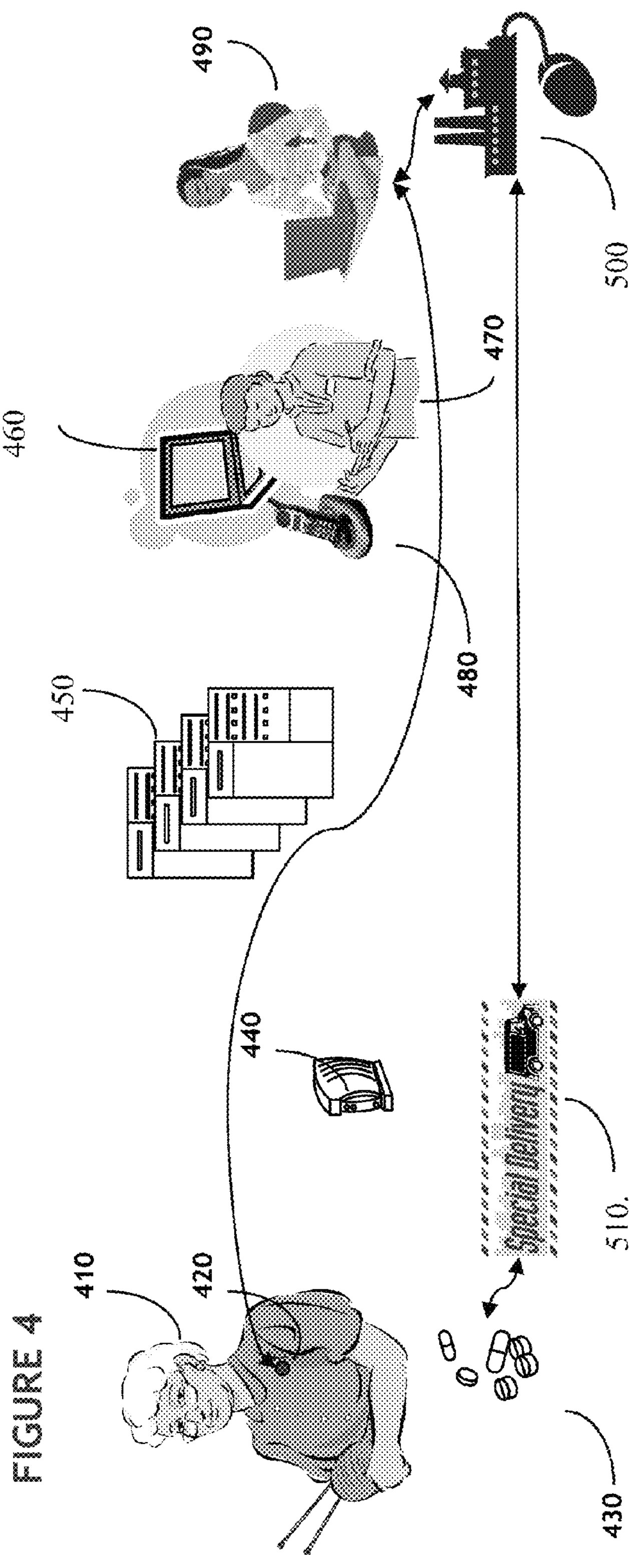
FIG. 4 depicts a system according to an embodiment of the invention for performing methods of the invention.

A specific representative embodiment of the above described methods and systems that may be employed in the management of a specific patient for a specific disease condition is depicted in FIG. 4. Patient 410 is a cardiovascular patient that may suffer from a variety of cardiovascular disease conditions, e.g., heart failure, hypertension, etc. Patient 410 has been implanted with a cardiovascular medical device, 420, which may include one or more of an electrical therapy element, a sensor element, including but not limited to the sensors described below, as well as a monitoring element. In certain embodiments, the monitoring element is configured to obtain, store and forward actual dosage administration information from an identifier tagged pharmaceutical composition, e.g., as described in PCT application serial no. PCT/US2006/016370 titled "Pharma Informatics System" which was filed on Apr. 28, 2006 and published as WO 2006/116718 on Nov. 2, 2006; as well as the additional embodiments of such smart dosages as described in U.S. Provisional Application Ser. Nos. 60/866,581; 60/829,832; 60/887,780; 60/889,868; 60/889,870; 60/889,871; 60/894,171 and 60/894,167; the disclosures of which applications are herein incorporated by reference. In addition, patient 410 is taking a plurality of different pharmaceuticals 430 according to a prescribed pharmaceutical dosage regimen. The pharmaceuticals 430 are identifier tagged pharmaceuticals, e.g., that include identifying IC chips that emit a signal upon contact with a target physiological site, as described in PCT application serial no. PCT/US2006/016370 titled "Pharma Informatics System" which was filed on Apr. 28, 2006 and published as WO 2006/116718 on Nov. 2, 2006; as well as the additional embodiments of such smart dosages as described in U.S. Provisional Application Ser. Nos. 60/866,581; 60/829,832; 60/887,780; 60/889,868; 60/889,870; 60/889,871; 60/894,171 and 60/894,167; the disclosures of which applications are herein incorporated by reference. Also shown in FIG. 4 is modem 440 that serves to relay obtained dosage information from the patient 410 to a remote location, e.g., a doctor's office. Modem 440 may be located at an in-home location, e.g., the bedside, and connected to Internet, e.g., via a wireless connection, so that data can be uploaded by the modem to the internet and designated address thereon automatically at a predetermined daily time, e.g., when the patient is expected to be near the modem, such as at 3 AM when the patient is expected to be asleep in their bed. Of course modem 440 may be replaced by any convenient communications element, such as a network relay station, etc. Of interest are embodiments where elements 430, 420 and 440 communicate via an implantable or topical signal receiver element (e.g., a personal health companion device) that is configured to detect dosage administration, e.g., by a signal emitted by an identifier of a pharma informatics enabled dosage formulation, such as described in pending provisional application Ser. No. 60/887,780 titled "Signal Receivers for Pharma-Informatics Systems"; the disclosure of which is herein incorporated by reference.

Central processor 450 includes servers that include or can access a number of different information sources, e.g., patient databases, population information, subpopulation information, patient specific information, etc. The dataset or sets present in processor 450 may be raw datasets or processed in some manner, e.g., to produce subsets or populations, e.g., categories of data. For example, compliance data from an individual patient over a period of time can be combined with data from other individuals. The combined data can be processed to identify trends or subpopulations of individuals that respond similarly under similar dosage compliance and/or other parameters, e.g., health, age, disease stage, etc. Trends or subpopulations may be identified from the raw data using any convenient protocols, including by use of data processing algorithms that can process the data automatically and identify trends or subpopulations, e.g., according to predetermined rules. The identified trends/subpopulations can then be employed in a variety of different ways, as desired. For example, information about a given population or groups of populations can be used by a health care professional to help inform a practitioner on the best way to treat a particular patient given that patients individual compliance data. For example, a health care professional, such as a pharmaceutical representative, can help nurse 470 and/or doctor 490 make informed therapeutic treatment regimen decisions for patient 410 by helping nurse 470 and/or doctor 490 to interpret the particular compliance data obtained from patient 410 in the context of a given subpopulation of patients as identified and available to the representative from datasets 450. In this manner nurse 470 and/or doctor 490 actively employ the sales representative and the knowledge provided to the sales representative from datasets 450 in making individual treatment therapeutic regimen decisions for patient 410.

Laptop 460 is an embodiment of the system 300 depicted in FIG. 3 and includes a decision support tool, such as a therapeutic regimen evaluator, as reviewed above. The decision support tool has access to a variety of different types of information, such as information provided in the database exemplified as element 450, information present in the doctor's office, e.g., patient records. In certain embodiments, the decision support tool 460 can complete prescription and/or generate E-mail alerts based on data. In certain embodiments, the decision support tool 460 is linked to a wider health or hospital information system.

Shown in FIG. 4 is nurse 470 that can review patient alerts and individual web pages, contact the patient or caregiver thereof, provide advice and/or schedule visits based on recommendations generated by the decision support tool, e.g., via phone 480.

In FIG. 4, doctor 490 performs one or more of the following tasks, e.g., reviews the patient log, adjusts electrical therapy, develops profiles, selects drug alternates, adjusts dosing, confirms that the current regimen is acceptable, etc. In the embodiment shown in FIG. 4, when the doctor adjusts dosing regimens, this information is forwarded to manufacturer 500. While a central manufacture is shown in FIG. 4, the dosing adjustment instructions could be forwarded to any convenient formulator, e.g., hospital or independent pharmacy, or even home formulation device. Manufacturer 500, in response to the dosing information provided by the doctor 490, makes drugs to order which are specifically tailored to the patient 410 as specified by doctor 490, e.g., within a 48 hour cycle. The manufactured physical dosage is then forwarded directly to the patient, e.g., by express mail, as depicted by element 510.

Programming

The invention also provides programming, e.g., in the form of computer program products, for use in practicing the methods. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM, ROM, flash drives, micro drives; and hybrids of these categories such as magnetic/optical storage media. One of skill in the art can readily appreciate how any of the presently known computer readable mediums can be used to create a manufacture that includes a recording of the present programming/algorithms for carrying out the above-described methodology.

Utility

The present invention provides the clinician an important new tool in their therapeutic armamentarium i.e., the ability to customize therapeutic regimens in a patient specific manner. The present invention allows therapeutic regimens to be developed and modified based on actual dosage administration information, which information can be supplemented with additional dosage relevant information, such as additional physiological parameters, lifestyle information, etc. In this manner, patient specific customized optimal therapeutic regimens may be formulated by the clinician. A number of benefits result from implementation of the present invention, including but not limited to one or more of: reduced medical errors, e.g., such as those that can arise from using a standardized therapeutic regimens in a variable compliance environment; a reduction in liability, since errors will be reduced; etc.

One type of application in which the subject compositions and systems find use is in monitoring patient compliance with prescribed therapeutic regimens. By monitoring patient compliance is meant tracking whether a patient is actually taking medication in the manner prescribed to the patient. As such, the present invention provides accurate data of when a pill has been taken and which pill has been taken. This allows the precise determination of which pill was taken at a specific point in time. Such monitoring capability assures patients are taking the prescribed medication correctly. This information avoids the potential for over prescription of medications that are not actually being taken. By example, if pain killers are intended to be administered to a patient, it is possible to verify with the present invention that the patient did in fact take those pain killers in a certain period of time. This knowledge is an important tool in limiting the illicit sale of unconsumed drugs to an unintended party. In the case of cardio vascular pills, the clinician or care giver is able to verify that the amount of the drug was taken has been taken at approximately the right point and time. Thus, the true efficacy of the drug can be accurately evaluated. Proper administration and patient compliance is especially critical in Alzheimer's, psychiatric, and alcohol aversion drugs, and in the treatment of rest home residents. In the case of accidental and other overdoses situations, the intervening clinician will be able to discern how far the ingestion has proceeded, and how many pills are involved.

In more complex embodiments of the present invention, correct, timely ingestion of the drugs will automatically trigger a prescription refill signal which is forwarded to a pharmacy data system, and in some cases the refill will be automatically delivered directly to the patient's home, or released by a device in the patient's home some period of time later. This feature is particularly valuable in patients with compromised mental capacity and/or limited physical mobility.

The invention is particularly useful in complex administration regimens, such as when multiple pharmaceuticals are being taken, and confusion is more likely to occur. The inventive pills can have multiple external layers, with only correct dosage allowing dissolution and absorption of the pharmaceutical component. Specific indicators, such as electrical conduction velocity in the heart or electrolytic levels in the blood in response to pharmaceutical can also be titrated.

In certain embodiments, a patient can be alerted when the patient is in some way non-compliant with a given treatment regimen. For example, by a sound, visual, or computer reminder, if the pharmacological regimen is not being accurately adhered to, a reminder is provided. If that reminder is not accurately responded to, the system can provide an alert to family members, caregivers, or clinicians in order to remedy the gap in treatment or overdose. The device may also automatically modify the dosage and timing of the regimen to compensate for prior non-standard dosing.

One type of application in which the subject compositions and systems find use is in tailoring therapeutic regimens based on patient compliance. In such applications, data obtained about whether a patient has or has not taken a particular dosage is employed to determine future dosages and/or timing of such dosages. In certain embodiments, data concerning patient compliance is combined with additional data, e.g., sensed physiological data, to make customized changes or modifications to a given therapeutic regimen. By example, when data about dosage compliance obtained according to the invention is used in concert with other medical sensing devices, correlation between drug delivery, batch and dosage can be correlated to a physiological response. In this manner, optimal pharma-therapeutic regimens may be formulated by the clinician. By example, cardiac stimulating drugs can be titrated to the most appropriate dosages, minimizing side effects such as cardiac muscle exhaustion and rebound effects among others, and optimizing both dosage and timing for each individual patient.

Assessment of a range of alternate medications is made possible by the present invention without resort to awaiting overt clinical sequel of treatment, many of which can be seriously adverse. By example, positive effects would be quickly ascertainable without being obscured by more random factors. Negative responses, such as changes in blood pressure, would become clearly evident as drug related or independent above background physiologic variation.

In one clinical arena, the present invention allows, in concert with other sensing devices developed by some of the present inventors, the measurement and assessment of the cardiac response to those medications. These co-employed sensing devices can be those enumerated below, among others. Other sensing technology, e.g., as mentioned above, developed by some of the present inventors allows measurement of heart health and cardiac efficiency. Using these tools in concert with the present inventive device, the clinician will be able to compare the response of the heart and body to the administered pharmaceutical. The data provided by the present invention can optionally be recorded over time. The recording system records synchrony or conduction velocity of a signal going through cardiac tissue and how that is mediated by the presence of a certain medication. These unique data are made possible by the present invention.

In more standard clinical environments, these unique data allow careful selection and titration of drug administration without resort to more overt physical symptoms to ascertain contraindications, efficacy, and optimal dosage levels. The present invention provides a record for emergency room technicians or doctors when a patient is admitted to a hospital so that the patient's status can be accurately ascertained. Dosage events within the last hour or day prior to admission, and the identity of the last medication, will be immediately available. As such, future therapeutic regimens can be made based on accurate records of patient drug medication history.

The patient monitoring capacity of the external reporting apparatus is an importation function which the inventive device can provide. When coordinated with internal or external physiologic sensing data, the device can read out the physiological response of the patient to the ingestion of medication, and then transmit this information back to the clinician. The clinician can then modify therapy to optimal effectiveness, as indicated by the new data in response to the modified therapy, and so forth.

In more sophisticated embodiments of the present invention, the dosage adjustment function, within certain parameters, can be performed by an intelligence circuit in the apparatus. By example, for a blood pressure medication, the patient takes their blood pressure pill. 20 minutes later, the internal monitoring circuitry in the implantable device registers a drop in blood pressure. The circuitry quantifies this drop, and transmits it to this bedside apparatus. The apparatus then can adjust the dosage of the pill to optimally treat the patient. Similarly, when the patient is connected to an IV, the dosage can be dispensed directly into the IV fluid. In certain embodiments, the closed-loop system is provided as a fully implantable device.

Current clinical practice for drug treatment optimization is considerably more limited than that which is available by use of the present inventive device. Currently, blood pressure medication treatment is set at so many pills per day. Such a blunt dosage regime takes a long time to optimize appropriately because the feedback loop is very slow. By contrast, with the present invention, the feedback loop of physiologic response to pharmaceutical dosage is very rapid and very efficient. Ultimately, the present invention allows tailoring the drug dosages day to day, or even more finely, to account for change in activity, change in physiological conditions in the patient, and other dosage parameter.

In more sophisticated embodiments of the present invention, physiological reactions to specific dosages and time intervals would also be continually monitored. In some embodiments, the level of drug in the blood stream is monitored, allowing for individual and time of day variations in drug metabolism.

This aspect of the present invention effectively minimizes underdosing or overdosing the controlled substances, in some cases addressing these changes before they produce external symptoms apparent to the patient or clinician. The drug dosage can be automatically titrated so that, by example, the smallest appropriate level to quell anxiety due to pain, other physiologic reactions to pain, or provide steady or gradually diminishing blood levels of the drug would be dispensed. This feature of the present invention provides an automatic, appropriately gradual, weaning off of the drug, lessening the chance of serious addiction or severe, adverse withdrawal reactions.

Kits

Also provided are kits for practicing the subject methods. Kits may include one or more components of the systems as described above, e.g., smart packaged dosages, smart pharmaceutical compositions, receivers and modems, computer programming, etc.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of managing a therapeutic regimen for treatment of a patient, the therapeutic regimen specifying a pharmaceutical dosage of the medical composition and a dosing schedule, the method comprising:

receiving confirmatory data from a first device associated with a patient at a second device associated with a body of the patient when the first device is ingested by the patient and is activated upon contact with an electrically conductive body fluid via completion of a partial power source, wherein the first device is electrically coupled to the body of the patient, wherein the confirmatory data represents actual ingestion of the pharmaceutical dosage of the medical composition by the patient, and wherein the confirmatory data is produced by the first device and is transmitted to the second device;

receiving at the second device physiological data indicating a response of the patient to the pharmaceutical dosage of the medical composition, wherein the second device is electrically coupled external to the body of the patient;

evaluating the confirmatory data and the physiological data to determine when a change in the therapeutic regimen is desired; and modulating the therapeutic regimen when the change is determined to be desired, wherein modulating the therapeutic regimen comprises changing at least one of the pharmaceutical dosage of the medical composition and the dosing schedule based on the evaluation of the confirmatory data and the physiological data.

2. The method according to claim 1, further comprising recording the confirmatory data by the second device.

3. The method according to claim 1, the first and second devices are electrically coupled to the body.

4. The method according to claim 1, further comprising transmitting a signal representative of the confirmatory data from the first device to the second device, wherein the signal is established by an electrical current between the first and second devices.

5. The method according to claim 4, further comprising confining the electrical current among the first and second devices and the body.

6. The method according to claim 4, further comprising confining the electrical current among the first and second devices, wherein the first and second devices are each capacitively coupled to a conductor or ground external to the patient.

7. The method according to claim 1, further comprising automatically receiving the confirmatory data at the second device.

8. The method according to claim 1, wherein the first and second devices are different types of devices.

9. The method according to claim 8, wherein the first device comprises an active agent.

10. The method according to claim 9, wherein the second device does not comprise an active agent.

11. The method according to claim 10, further comprising transmitting a second set of confirmatory data from a third device to the second device.

12. The method according to claim 11, wherein the third device comprises an active agent.

13. The method according to claim 1, wherein the medical composition is selected from the group consisting of a drug, a vitamin, saline, infusate, a dialysate and an antacid.

14. The method according to claim 1, wherein the first device comprises an identifier associated with a pharmaceutical composition, the method further comprising producing the confirmatory data by the identifier upon contact with a target physiological site of the patient.

15. The method according to claim 1, wherein the evaluating comprises inputting the data into a decision support tool and obtaining from the decision support tool a recommendation based on the confirmatory data as to whether a change in the therapeutic regimen is desirable.

16. The method according to claim 15, wherein the evaluating further comprises assessing lifestyle information obtained from the patient.

17. The method according to claim 15, further comprising determining whether a change in the therapeutic regimen is to be made.

18. The method according to claim 17, further comprising preparing a physical pharmaceutical dosage of the medical composition and forwarding the physical pharmaceutical dosage to the patient, wherein the physical pharmaceutical dosage comprises at least one active agent.

19. The method according to claim 18, wherein the physical pharmaceutical dosage comprises two or more distinct compositions.

20. The method according to claim 18, wherein the physical pharmaceutical dosage comprises at least one composition that includes at least two active agents.

21. The method according to claim 20, wherein the at least one composition is fabricated in response to the modulation of the therapeutic regimen.

22. The method according to claim 20, wherein the at least one composition of the physical pharmaceutical dosage comprises a dosage actual ingestion compliance identifier.

23. The method according to claim 17, further comprising modulating the therapeutic regimen and communicating a modulated therapeutic regimen to the patient.

24. The method according to claim 23, wherein modulating the therapeutic regimen comprises changing pharmaceutical dosage of the medical composition.

25. The method according to claim 24, further comprising changing an amount of a pharmaceutical agent.

26. The method according to claim 24, wherein modulating the therapeutic regimen further comprises changing at least one type of pharmaceutical agent administered to the patient.

27. The method according to claim 1, further comprising forwarding the confirmatory data from the patient to a location distinct from the second device location.

28. The method according to claim 27, wherein the location distinct from the second device location is a remote location.

29. The method of claim 1, further comprising establishing an electrical current between the first and second devices to transmit the confirmatory data therebetween, wherein the body of the patient serves as a conductive medium through which the electrical current travels to provide for communication between the first and second devices.

30. A system for managing a therapeutic regimen for treatment of a patient, the therapeutic regimen specifying a pharmaceutical dosage of the medical composition and a dosing schedule, the system comprising:

(a) an input manager for receiving:

confirmatory data for actual ingestion of a medical composition by a patient from a first device when the first device is ingested by the patient and is activated upon contact with an electrically conductive body fluid via completion of a partial power source, wherein the first device is electrically coupled to the body of the patient, wherein the confirmatory data represents the actual ingestion of the pharmaceutical dosage of the medical composition by the patient; and physiological data indicating a response of the patient to the pharmaceutical dosage of the medical composition from a second device, wherein the second device is electrically coupled external to the body of the patient, wherein communication from the first device to the second device is by way of a conductive current signal through a body of the patient, and wherein the second device is electrically coupled external to the body of the patient;

(b) a processing module comprising a therapeutic regimen evaluator configured to assess a therapeutic regimen based on received confirmatory data and the physiological data to determine whether a change in a therapeutic regimen is desirable and provide a recommendation based on the determination; and (c) an output manager for providing the recommendation to a user, wherein the recommendation indicates a change in at least one of the pharmaceutical dosage of the medical composition and the dosing schedule.

31. The system of claim 30, further comprising establishing an electrical current between a first device and a second device to transmit the confirmatory data therebetween, wherein a body of the patient serves as a conductive medium through which the electrical current travels to provide for communication between the first and second devices.

32. A method of treating a patient for a condition, the method comprising:

inputting confirmatory data received from the patient into a system, the system comprising:

(a) an input manager for receiving:

confirmatory data for actual ingestion of a medical composition by a patient from a first device when the first device is ingested by the patient and is activated upon contact with an electrically conductive body fluid via completion of a partial power source, wherein the first device is electrically coupled to the body of the patient, and wherein the confirmatory data represents the actual ingestion of the pharmaceutical dosage of the medical composition by the patient, and wherein the second device is electrically coupled external to the body of the patient; and physiological data indicating a response of the patient to the pharmaceutical dosage of the medical composition from a second device, wherein the second device is electrically coupled external to the body of the patient, wherein communication from the first device to the second device is by way of a conductive current signal through a body of the patient;

(b) a processing module comprising a therapeutic regimen evaluator configured to assess a therapeutic regimen based on received confirmatory data and the physiological data to determine whether a change in a therapeutic regimen is desirable and provide a recommendation based on the determination; and (c) an output manager for providing the recommendation to a user, wherein the recommendation indicates a change in at least one of the pharmaceutical dosage of the medical composition and the dosing schedule; and obtaining a recommendation from the system and treating the patient according to the recommendation.

33. A method in the form of a computer readable medium embodying a set of instructions that, when executed by a processor, causes the processor to perform the method of:

receiving confirmatory data for actual ingestion of a pharmaceutical dosage of a medical composition to a patient from a first device, when the first device is ingested by the patient and is activated upon contact with an electrically conductive body fluid via completion of a partial power source, wherein the first device is electrically coupled to the body of the patient;

receiving physiological data indicating a response of the patient to the pharmaceutical dosage of the medical composition, by a second device, wherein the second device is electrically coupled external to the body of the patient;

assessing a therapeutic regimen of the patient in view of the confirmatory data and the physiological data to determine whether a change in a therapeutic regimen is desirable; and providing the recommendation to a user, wherein the recommendation indicates a change in at least one of the pharmaceutical dosage of the medical composition and a dosing schedule based on the assessing.

34. A system comprising:

a first device configured to produce confirmatory data for actual ingestion of a pharmaceutical dosage of a medical composition to a patient and transmit the confirmatory data to a second device when the first device is ingested by the patient and is activated upon contact with an electrically conductive body fluid via completion of a partial power source, wherein the first device is electrically coupled to the body of the patient;

a second device configured to receive the confirmatory data from the first device and to receive physiological data indicating a response of the patient to the pharmaceutical dosage of the medical composition, wherein the second device is electrically coupled external to the body of the patient, wherein communication from the first device to the second device is by way of a conductive current signal through a body of the patient, and wherein the second device is electrically coupled external to the body of the patient; and a wireless communication device configured to receive the confirmatory data and the physiological data from the second device and to relay the received confirmatory data and the physiological data to a remote location.

35. The system according to claim 34, wherein the system further includes a device to process the confirmatory data and the physiological data and provide a recommendation to a user.

36. The system according to claim 34, wherein the first and second devices are configured to be associated with the body of a patient.

37. The system according to claim 34, wherein the first device comprises an active agent.

38. The system according to claim 34, wherein the remote location comprises a database.

39. The system of claim 34, wherein an electrical current is established between the first device and the second device to transmit the confirmatory data therebetween, wherein a body of the patient serves as a conductive medium through which the electrical current travels to provide for communication between the first and second devices.

* * * * *